US012569579B2

(12) United States Patent

Su et al.

(10) Patent No.: US 12,569,579 B2
(45) Date of Patent: Mar. 10, 2026

(54) ADULT TOY DISINFECTION DEVICE AND ADULT TOY

(71) Applicant: DONGGUAN YANSHI ELECTRONIC TECHNOLOGY CO., LTD., Dongguan (CN)

(72) Inventors: Yanyan Su, Hefei (CN); Wenqiang Wu, Jingzhou (CN)

(73) Assignee: DONGGUAN YANSHI ELECTRONIC TECHNOLOGY CO., LTD., Dongguan (CN)

( * ) Notice: Subject to any disclaimer, the term of this patent is extended or adjusted under 35 U.S.C. 154(b) by 0 days.

(21) Appl. No.: 19/280,623

(22) Filed: Jul. 25, 2025

(65) Prior Publication Data

US 2026/0027245 A1 Jan. 29, 2026

(30) Foreign Application Priority Data

Jul. 29, 2024 (CN) .......................... 202411029062.5

(51) Int. Cl.
*A61H 19/00* (2006.01)
*A61H 23/02* (2006.01)
(Continued)

(52) U.S. Cl.
CPC ................ *A61L 2/08* (2013.01); *A61H 19/44* (2013.01); *A61H 23/02* (2013.01); *A61L 2/24* (2013.01); *A61L 2/26* (2013.01); *A61H 2201/0153* (2013.01); *A61H 2201/50* (2013.01); *A61L 2202/11* (2013.01); *A61L 2202/121* (2013.01);
(Continued)

(58) Field of Classification Search
CPC . A61H 19/40; A61H 9/34; A61H 9/30; A61H 9/40; A61H 19/34; A61H 19/30; A61L 2/10
See application file for complete search history.

(56) References Cited

U.S. PATENT DOCUMENTS 4,888,487 A * 12/1989 Ritter ........................ A61L 2/10
250/455.11
10,959,907 B2 * 3/2021 Haddock ................ A61H 19/40
(Continued)

FOREIGN PATENT DOCUMENTS

| CN | 206842116 U | 1/2018 |
| CN | 119488618 A | 2/2025 |

*Primary Examiner* — Donald R Spamer
(74) *Attorney, Agent, or Firm* — Ming Jiang; OPENPTO US LLC

(57) ABSTRACT

An adult toy disinfection device and an adult toy are provided. The adult toy disinfection device includes a protective shell with an opening, where an inner cavity of the protective shell is a disinfection cavity. The adult toy disinfection device includes a disinfection spectrum generation assembly and a first driving assembly. At least a portion of the adult toy to be disinfected may be placed in the disinfection cavity through the opening, and the first driving assembly is electrically connected to the disinfection spectrum generation assembly and configured to drive the disinfection spectrum generation assembly to generate a disinfection spectrum. The disinfection spectrum generation assembly is disposed on an inner side of the disinfection cavity, such that the disinfection spectrum directly irradiates or indirectly irradiates a space of the disinfection cavity by means of an optical path.

18 Claims, 12 Drawing Sheets

(51) Int. Cl.
    *A61L 2/08*       (2006.01)
    *A61L 2/10*       (2026.01)
    *A61L 2/24*       (2006.01)
    *A61L 2/26*       (2006.01)

(52) U.S. Cl.
    CPC ..... *A61L 2202/122* (2013.01); *A61L 2202/16*
                                  (2013.01)

(56) References Cited

U.S. PATENT DOCUMENTS

| | | | |
|---|---|---|---|
| 11,259,987 B1 * | 3/2022 | Chen ...................... | A61H 19/34 |
| 2020/0179543 A1 * | 6/2020 | Deshays ................... | A61L 2/24 |
| 2022/0087896 A1 * | 3/2022 | Tai ......................... | A61H 19/44 |
| 2022/0193280 A1 * | 6/2022 | James ....................... | A61L 9/20 |
| 2024/0207475 A1 * | 6/2024 | Kaler ....................... | A61L 9/20 |

* cited by examiner

ADULT TOY DISINFECTION DEVICE AND ADULT TOY

CROSS REFERENCE TO RELATED APPLICATIONS

The present disclosure claims priorities of Chinese Patent Application No. 202411029062.5, filed on Jul. 29, 2024, the entire contents of which are hereby incorporated by reference.

TECHNICAL FIELD

The present disclosure relates to the technical field of sex toys, and particularly relates to an adult toy disinfection device and an adult toy.

BACKGROUND

As people are increasingly open-minded and pursue improvement in the quality of life, adult toys, as tools that meet personal privacy needs and relieve life pressure, are increasingly popular among people. Such products are in direct contact with private parts of human body during use, and after use, surfaces thereof are easily contaminated with body fluids such as skin secretions and sweat.

However, most adult toys in the prior art are cleaned by users manually, which is not only cumbersome to operate but also difficult to ensure thorough cleaning, resulting in that residual body fluids create a breeding ground for the growth of microorganisms such as bacteria and molds. Improper cleaning for a long time causes the proliferation of massive microorganisms, which not only contaminates the product but also causes cross-infection during subsequent use, thereby posing a potential threat to the user's health and seriously affecting the safety and experience of use.

Currently, few specialized disinfection devices for adult toys are available on the market, toys of some materials may be corroded when disinfection methods in the prior art such as alcohol wiping are adopted, and it is difficult to achieve the comprehensive and thorough disinfection. Therefore, it is necessary to develop a dedicated device capable of conveniently, efficiently, and safely disinfecting adult toys so as to solve the safety problems existing in the above adult toys.

SUMMARY

In view of the above problems, an objective of the present disclosure is to provide an adult toy disinfection device capable of comprehensively and efficiently disinfecting adult toys, so as to solve the above problems.

The present disclosure is achieved by means of the following technical solution:

In a first aspect, the present disclosure provides an adult toy disinfection device, and the adult toy disinfection device includes a protective shell with an opening, where an inner cavity of the protective shell is a disinfection cavity, and the adult toy disinfection device includes a disinfection spectrum generation assembly and a first driving assembly; at least a portion of the adult toy to be disinfected may be placed in the disinfection cavity through the opening; the first driving assembly is electrically connected to the disinfection spectrum generation assembly and configured to drive the disinfection spectrum generation assembly to generate a disinfection spectrum; and the disinfection spectrum generation assembly is disposed on an inner side of the disinfection cavity, such that the disinfection spectrum directly irradiates or indirectly irradiates a space of the disinfection cavity by means of an optical path.

According to the technical solutions in the embodiments of the present disclosure, after using the adult toy, the user simply rinses a surface of the adult toy to remove obvious residues, and then places a portion of the adult toy to be disinfected (usually the portion in contact with the user's body) into the disinfection cavity of the device through the opening. The disinfection spectrum generation assembly starts working and generates light with strong bactericidal and disinfection effects, and the light directly irradiates or indirectly irradiates an inner space of the disinfection cavity and a surface of the adult toy, to efficiently kill bacteria, viruses, molds, and other microorganisms in the residues such as skin secretions and sweat on the surface of the adult toy. The adult toy disinfection device provided by the present disclosure, by utilizing the strong bactericidal capability of specific spectra, is capable of thoroughly killing various pathogenic microorganisms (such as bacteria, viruses, mold spores, and the like) attached to the surface of the adult toy, which solves the problem that microbial residues cannot be completely removed through manual cleaning, and reduces the risks of microbial growth, product contamination, and cross-infection caused by incomplete cleaning. The user only needs to simply place the adult toy and start the disinfection device provided by the present disclosure, without need of cumbersome manual scrubbing, wiping, and worry about incomplete rinsing. High automation significantly reduces the cleaning burden and enhances the user convenience and pleasure. Compared with chemical disinfection methods such as alcohol wiping, physical disinfection with light of specific wavelengths does not cause adverse effects such as corrosion, dissolution, aging, or texture change of common adult toy materials such as silicone, a thermoplastic elastomer (TPE), and Acrylonitrile Butadiene Styrene (ABS) plastic, thereby ensuring the service life and safety of the adult toy.

In some embodiments, the disinfection cavity is provided with a spectral reflection layer; and the spectral reflection layer is disposed on an inner surface of the disinfection cavity and configured to reflect the disinfection spectrum.

According to the technical solutions in the embodiments of the present disclosure, during the disinfection of the adult toy, the disinfection spectrum generation assembly generates a disinfection spectrum, part of the disinfection spectrum directly irradiates the surface of the adult toy, and the remaining part of the disinfection spectrum irradiates the inner surface of the disinfection cavity. Since the inner surface of the disinfection cavity is covered with the spectral reflection layer, the remaining part of the disinfection spectrum is efficiently reflected back, and the reflected disinfection spectrum irradiates the inner space of the cavity and the surface of the adult toy again. This process will occur repeatedly (light "bounces" between reflection layers) until the energy is absorbed or attenuated. As a result, portions of the adult toy originally in shadow areas not directly irradiated by the light (such as a recessed portion of the adult toy, and an interior of the gap) are irradiated by the light reflected for many times, thereby reducing dead zones of disinfection. The spectral reflection layer reduces the ineffective absorption and loss of light on the cavity wall, and limits more light energy in the cavity and guides the same to the surface of the adult toy to be disinfected. Equivalently, an effective light dose is increased, thereby improving the microbial killing rate and achieving the more thorough disinfection effect within the same time.

In some embodiments, the spectral reflection layer has a diffuse reflection structure configured to achieve diffuse reflection of the disinfection spectrum that irradiates the inner surface of the disinfection cavity.

According to the technical solutions in the embodiments of the present disclosure, when the disinfection spectrum irradiates the spectral reflection layer with the diffuse reflection structure, the light scatters in all directions (at all angles), and diffusely reflected light fills the entire disinfection cavity to form a highly uniform and non-directional light field environment, and the scattered light from all directions irradiates all exposed surfaces of the adult toy, such that all surfaces of the adult toy receive sufficient and similar disinfection doses. The scattered light easily bypasses obstacles and penetrates into recessed portions, holes, thread gaps, and shadow areas formed due to self-occlusion by the adult toy, that are hardly exposed to direct light, thereby further reducing the dead zones of disinfection. Additionally, when the scattered light encounters any other cavity wall or the surface of the adult toy, the light will undergo diffuse reflection again, and this process continues until the energy is attenuated. The superposition of multiple diffuse reflections further enhances the uniformity of the light field and the capability to cover dead zones.

In some embodiments, the device further includes a light guide assembly including an incident port, an optical path, and an exit port; the light guide assembly is disposed in the disinfection cavity, and the incident port is disposed at the disinfection spectrum generation assembly; one or more exit ports are disposed at one or more key disinfection portions of the adult toy; and the optical path is configured to guide the disinfection spectrum incident from the incident port to exit through the exit port.

According to the technical solutions in the embodiments of the present disclosure, after the adult toy is placed in the disinfection cavity, the key disinfection portions are aligned with the exit ports of the light guide assembly, the disinfection spectrum generation assembly starts working to generate a disinfection spectrum, part of the disinfection spectrum directly irradiates or indirectly irradiates an outer surface of the adult toy, and the remaining part of the disinfection spectrum enters the incident port of the light guide assembly; and the light entering the light guide assembly is transmitted through the optical path in a guided manner and finally emitted from one or more exit ports of the light guide assembly, the exit ports are pre-designed to be aligned with the key disinfection portions of the adult toy, the light directly, closely and intensively irradiates the key disinfection portions, and the light guide assembly actively delivers and injects the disinfection spectrum into the shadow areas, which reduces the dead zones of disinfection, and achieves deep disinfection. Through the light guide assembly, the disinfection spectrum accurately hits the target, prevents energy waste in non-target areas, and enhances the thoroughness and reliability of disinfection of the key disinfection portions. Precisely targeting the portions most difficult to be disinfected prevents long-time and high-intensity excessive irradiation of the entire adult toy performed to ensure the safety of the portions, thereby shortening the overall disinfection time or reducing the power of the disinfection spectrum generation assembly.

In some embodiments, the device further includes a first motion platform carrying the light guide assembly for motion.

According to the technical solutions in the embodiments of the present disclosure, one (or a few) exit port of the light guide assembly, driven by the first motion platform, efficiently and sequentially covers a plurality of key disinfection portions at different positions of the adult toy. There is no need to separately design fixed exit ports for each portion, which simplifies the structure, reduces costs, and improves versatility. When any adult toy is placed in the cavity in any manner, the first motion platform adjusts a position and angle of the exit port of the light guide assembly to find and accurately irradiate the key disinfection portions, thereby adapting to adult toys of different shapes at any positions and angles.

In some embodiments, the first driving assembly has a first disinfection driving strategy; the first disinfection driving strategy includes a first driving program implemented by software and/or hardware circuits; and the first driving program is configured to drive a plurality of the disinfection spectrum generation assemblies corresponding to a plurality of the key disinfection portions to light up one by one.

According to the technical solutions in the embodiments of the present disclosure, a plurality of the disinfection spectrum generation assemblies corresponding to a plurality of the key disinfection portions are generally connected to the power supply through the same wire, and when a plurality of high-power assemblies (i.e., the disinfection spectrum generation assemblies) are lit up simultaneously, total working current is extremely large. A larger current I indicates a greater voltage drop (voltage loss) caused by a resistance R of the wire, which results in that an actual working voltage of the assembly away from the power supply is significantly lower than a nominal value. The strategy of lighting up the disinfection spectrum generation assemblies one by one ensures that only a single disinfection spectrum generation assembly works at any time, thereby significantly reducing the working current I (only the working current of a single disinfection spectrum generation assembly). Therefore, the voltage drop on the wire is reduced, and even when a longer or thinner wire is used, it is ensured that each assembly obtains a stable working voltage close to the voltage of the power supply during operation. An output wavelength of the disinfection spectrum generation assembly is extremely sensitive to the working voltage. Minor fluctuations in the voltage (caused by the line loss or power supply fluctuations) cause wavelength shifts, and the strategy of lighting up the disinfection spectrum generation assemblies one by one provided by the present disclosure ensures that each of the disinfection spectrum generation assemblies works at a stable optimal voltage during the working period, and outputs an accurate and stable target disinfection spectrum, thereby ensuring the highest disinfection efficiency.

In some embodiments, the device further includes a light condensing member and a light scanning assembly; the disinfection spectrum forms a focused light spot through the light condensing member, and the light scanning assembly is configured to cause the focused light spot of the disinfection spectrum to perform scanning motion in an area A; and the area A covers an area of the adult toy to be disinfected.

According to the technical solutions in the embodiments of the present disclosure, when the disinfection spectrum generation assembly works, the generated disinfection spectrum first passes through the light condensing member, the light condensing member converges the originally divergent light to form a focused light spot with a significantly higher energy density and smaller size, and the light scanning assembly drives the high-energy focused light spot to perform fast and controllable motion (i.e., scanning) in the pre-defined or intelligently recognized area A. The area A is designed to cover the entire portion of the adult toy to be disinfected in the disinfection cavity. The disinfection device provided by the present disclosure concentrates the limited light source energy on an extremely small area through the light condensing member, such that the energy density (light power per unit area) at the light spot is increased, thereby improving the disinfection effect on the irradiated area. Since energy is highly concentrated on the points that need to be disinfected and is not evenly dispersed, an overall energy utilization rate of the disinfection spectrum is improved. Additionally, although the energy at the light spot is relatively high, the light scanning assembly causes the light spot to dwell at a single point for a short time, resulting in that the heat does not accumulate significantly before the light spot moves away. Therefore, even when a higher-power light source is used, the risk of overheating, melting or accelerated photoaging of the surface of the adult toy caused by long-time irradiation is effectively prevented.

In some embodiments, a plurality of the disinfection spectrum generation assemblies form a focused light spot through the same light condensing member.

According to the technical solutions in the embodiments of the present disclosure, the power of a single disinfection spectrum generation assembly is limited, an energy density of the focused light spot has an upper limit, and when the light energy of the plurality of the disinfection spectrum generation assemblies is converged onto the same tiny light spot through a same optical system, a peak energy density (light power per unit area) of the light spot is multiplied, and the light spot has stronger instantaneous disinfection capability. Higher energy density means that the dwell time of the light spot required to achieve the same disinfection dose is shorter, or a coverage frequency in the same time is increased, which speeds up the overall disinfection. Additionally, a plurality of small light sources are converged by the same light condensing member to form a light spot with a size equivalent to or even smaller than that focused by a single light source, which prevents the problem of light spot enlargement and limited energy density increase caused by simply increasing the power of the light source, and ensures that the light spot with the strong disinfection capability accurately acts on various small structures on the surface of the adult toy.

In some embodiments, the light scanning assembly is a second motion platform carrying the disinfection spectrum generation assembly for motion.

According to the technical solutions in the embodiments of the present disclosure, the second motion platform, as the light scanning assembly, drives the disinfection spectrum generation assembly to move in the disinfection cavity according to a predetermined trajectory. Since the light condensing member is relatively fixed to the disinfection spectrum generation assembly, when the platform moves, the focused light spot emitted by the light condensing member changes in an irradiation point with the positional change of the disinfection spectrum generation assembly, thereby completing the scanning motion in the area A and achieving full coverage of the portions of the adult toy to be disinfected.

In some embodiments, the disinfection cavity includes an exhaust assembly; and water vapor inside the disinfection cavity is discharged outside the disinfection cavity through the exhaust assembly.

According to the technical solutions in the embodiments of the present disclosure, the adult toy may be simply cleaned before being placed into the disinfection cavity, and residual water on the surface of the adult toy may remain inside the cavity, which will form a humid environment and a new breeding ground for the growth of bacteria and molds, such that even after disinfection, microorganisms reproduce again due to humidity. The exhaust assembly timely discharges the water vapor formed after water volatilization, to keep the cavity dry, eliminate the risk of secondary contamination caused by humidity, and consolidate the disinfection effect. Furthermore, a humid environment affects the performance of electronic elements and mechanical structures such as the disinfection spectrum generation assembly (e.g., causing short circuits and rusting of metal components), and the exhaust assembly prolongs the service life of each assembly of the device and reduces the probability of failure by maintaining the dryness of the cavity.

In some embodiments, the device further includes a disinfection indication assembly; the disinfection indication assembly includes a light-emitting unit; and the light-emitting unit is in an operating state during the disinfection process.

According to the technical solutions in the embodiments of the present disclosure, on the one hand, the operating state of the light-emitting unit enables the user to quickly know that the disinfection device is working, which prevents accidental shutdown or premature removal of the adult toy and ensures the complete execution of the disinfection process; and on the other hand, during the disinfection process, the operating state of the light-emitting unit indirectly reminds the user of high energy inside the disinfection device, which prevents the user from opening the cavity and be exposed to the disinfection spectrum in this case, thereby reducing the risk of accidental injury.

In some embodiments, the operating state is one or more of breathing flash, color gradient flash, and chasing light flash.

According to the technical solutions in the embodiments of the present disclosure, compared with single continuous illumination or regular flashing, the above three illumination modes have higher visual distinctiveness, thereby making it easier to attract the user's attention and play a prompting role. Different illumination modes correspond to different disinfection stages or enable to distinguish the working states of different spectra, thereby achieving more meticulous information transmission for the user.

In a second aspect, the present disclosure provides an adult toy, and the adult toy includes a housing, a battery, and a control circuit, further including a disinfection device, a vibration massage assembly, and a second massage assembly; the battery, the control circuit, and the massage assemblies are electrically connected; the disinfection device includes a disinfection spectrum generation assembly, a first driving assembly, and a protective shell with an opening, where an inner cavity of the protective shell is a disinfection cavity; the vibration massage assembly and the second massage assembly may be placed in the disinfection cavity through the opening, and the housing and the protective shell may be combined to form an enclosed cavity; and the disinfection spectrum generation assembly is disposed on an inner side of the disinfection cavity, and the first driving assembly is configured to drive the disinfection spectrum generation assembly to generate a disinfection spectrum irradiating the space of the disinfection cavity.

According to the technical solutions in the embodiments of the present disclosure, after using the vibration massage assembly and the second massage assembly of the adult toy provided by the present disclosure, the user resets the vibration massage assembly and the second massage assembly from the working position, then places them into the disinfection cavity through the opening, and pushes the housing and the protective shell together to form the enclosed cavity. After the disinfection function is activated, the first driving assembly drives the disinfection spectrum generation assembly to generate a disinfection spectrum, the disinfection spectrum irradiates the enclosed space of the disinfection cavity to disinfect the surfaces of the vibration massage assembly and the second massage assembly, and after completion of the disinfection process, a power supply of the first driving assembly is disconnected, and the housing and the protective shell protect the vibration massage assembly and the second massage assembly until the user uses them next time. The adult toy provided by the present disclosure integrates the disinfection device and the massage assemblies, and the adult toy is directly disinfected after use for storage, which eliminates the cumbersome process of separately cleaning and disinfecting the adult toy after massage, and enhances the use convenience of the adult toy. The enclosed cavity formed by the combination of the housing and the protective shell not only prevents the leakage of the disinfection spectrum (thereby protecting the user), but also ensures that the disinfection spectrum reflects and circulates in the enclosed cavity, thereby enhancing the disinfection coverage of the surfaces and gaps of the vibration massage assembly and the second massage assembly, and achieving more thorough disinfection than that in an open environment. The vibration massage assembly and the second massage assembly may be directly stored in the enclosed cavity formed by the combination of the housing and the protective shell, which prevents the scattering or loss of assemblies, and facilitates storage and carrying due to an overall compact structure.

In some embodiments, the housing includes a first connecting portion; and the vibration massage assembly is detachably connected to the housing through the first connecting portion.

According to the technical solutions in the embodiments of the present disclosure, the vibration massage assembly needs to be in close contact with the human body during use, and after being disassembled from the housing, the vibration massage assembly may be flexibly inserted into private spaces such as vagina and rectum due to a smaller size, to directly act on sensitive areas in the body. Compared with the design of integration with the housing, the assembly disassembled better fits a curve of an internal physiological structure, and achieves more precise touch of target points during massage, thereby enhancing the pertinence and comfort of massage, and meeting the needs of internal massage.

In some embodiments, the vibration massage assembly includes a second connecting portion; and the second connecting portion flexibly connects the vibration massage assembly to the housing, and the vibration massage assembly may be pulled through the second connecting portion.

According to the technical solutions in the embodiments of the present disclosure, in actual use, when the user disassembles the vibration massage assembly from the housing, the second connecting portion remains flexibly connected to the vibration massage assembly, then the disassembled vibration massage assembly is slowly placed into the target area such as the vagina or rectum, and in this process, an angle of insertion of the vibration massage assembly is adjusted by gently pulling the second connecting portion. During massage, when a positional shift is felt, the vibration massage assembly is pulled through the second connecting portion to fine-tune the position of the vibration massage assembly. After the massage, the vibration massage assembly is slowly removed from the body through the second connecting portion, to prevent discomfort caused by directly pulling out the vibration massage assembly. Then the vibration massage assembly is placed into the disinfection cavity, and the housing and the protective shell are combined for disinfection. The pulling operation is not complex, and is completed only by holding the housing and pulling the second connecting portion, which addresses the inconvenience of adjusting the position of the vibration massage assembly in the body. During the whole massage process, the vibration massage assembly is always connected to the housing through the second connecting portion, which prevents the risk of hardly taking out the vibration massage assembly in the human body due to deep insertion, thereby enhancing the safety of use.

In some embodiments, the second connecting portion includes a wire; and the wire is configured to electrically connect the vibration massage assembly to the control circuit.

According to the technical solutions in the embodiments of the present disclosure, the wire achieves both electrical connection and flexible pulling functions, prevents a dual structure of integrating a separate wire and an independent pulling rope, reduces connecting components between the vibration massage assembly and the housing, reduces the risk of entanglement, and simplifies the operation. The direct connection through the wire ensures continuous stability of the power supply and control signals during movement and position adjustment of the vibration massage assembly, and prevents sudden power outage or mode switching, thereby enhancing the use reliability.

In some embodiments, the vibration massage assembly is of an insertable egg-shaped vibrator structure.

According to the technical solutions in the embodiments of the present disclosure, a compact shape of the insertable egg-shaped vibrator adapts well to an internal space of human body, compared with other massage structures, the insertable egg-shaped vibrator facilitates deeper insertion without foreign body sensation, and a vibration source is close to a sensitive area, which reduces energy loss, achieves the more concentrated massage effect, and solves the problem of discomfort when a large assembly is inserted into the body. Additionally, a surface of the egg-shaped vibrator structure is smooth without dead zones, and after the egg-shaped vibrator is placed into the disinfection cavity, the spectrum uniformly irradiates curved surfaces and gaps, which ensures the safety for the next use.

In some embodiments, the first connecting portion is a cavity with a single open end, and the vibration massage assembly is connected to the housing in a way of being inserted into the cavity; and after the vibration massage assembly is inserted into the cavity, a massage portion of the vibration massage assembly protrudes from the cavity and achieves a massage function.

According to the technical solutions in the embodiments of the present disclosure, the first connecting portion is a cavity with a single open end, and the exposed massage portion retains the full functionality after the vibration massage assembly is inserted into the cavity, such that the vibration massage assembly massages the user's body in the state of being inserted into the cavity. The cavity with the single open end achieves connection through the embedded fitting of the vibration massage assembly, and during vibration, a friction between the vibration massage assembly and an inner wall of the cavity offsets a vibration impact force, which reduces the risk of loosening; and additionally, disassembly operations are not complex, but are simple, practical, and convenient, and direct insertion and removal are allowed.

In some embodiments, the second massage assembly is fixedly connected to the housing, and the second massage assembly includes a swinging blade and a second driving assembly; and the second driving assembly drives the swinging blade to swing to massage the user's massage area.

According to the technical solutions in the embodiments of the present disclosure, the swinging blade is designed as a small-volume structure shaped like a tongue tip or an ellipse, with thin and rounded edges. Upon activation, the second driving assembly controls the swinging blade to perform the low-amplitude high-frequency swinging operation, and a swinging trajectory simulates the licking and sweeping actions of the tongue, and fits the user's sensitive body surface areas such as the neck, areas behind the ears, and inner thighs, thereby achieving a delicate massage experience similar to tongue licking. The lightweight design of the small-volume blade reduces the pressure on the skin, and offers a soft and smooth touch experience similar to that of the human tongue due to use of a super-soft silicone material; and the high-frequency small-amplitude swinging restores the flexible rhythm of tongue licking, which stimulates more real experience of natural human contact and reduces the mechanical stiffness during operation.

In some embodiments, the second massage assembly further includes a contact ring wall; the contact ring wall is connected to the housing; and the swinging blade is disposed at a bottom of the contact ring wall.

According to the technical solutions in the embodiments of the present disclosure, the contact ring wall with an annular contour fits the skin, limits a motion range of the swinging blade, prevents the situation that the swinging blade deviates from a target area during high-frequency swinging, and especially for an arc-shaped or irregular body surface, a framing effect of the contact ring wall ensures that the swinging blade always acts on a core massage point. The contacts of the contact ring wall provide surrounding static or dynamic pressure stimulation, and the multi-layered sensation of peripheral wrapping and central tongue licking is formed together with the tongue-licking dynamic stimulation of the central swinging blade, which simulates the real massage experience of lip wrapping and tongue licking, enhances the richness of skin touch, and improves the authenticity of the bionic experience.

Additional aspects and advantages of the present disclosure will be set forth partially in the following description, which will become obvious in the following description, or may be learned by practice of the present disclosure.

BRIEF DESCRIPTION OF THE DRAWINGS

To describe the technical solution in the embodiments of the present disclosure more clearly, the accompanying drawings required for describing the embodiments are briefly described below. It is to be understood that the following accompanying drawings show merely some embodiments of the present disclosure, and therefore it is not to be construed as a limitation to the scope. Those of ordinary skill in the art can also derive other accompanying drawings from these accompanying drawings without making inventive efforts.

Figure 1:
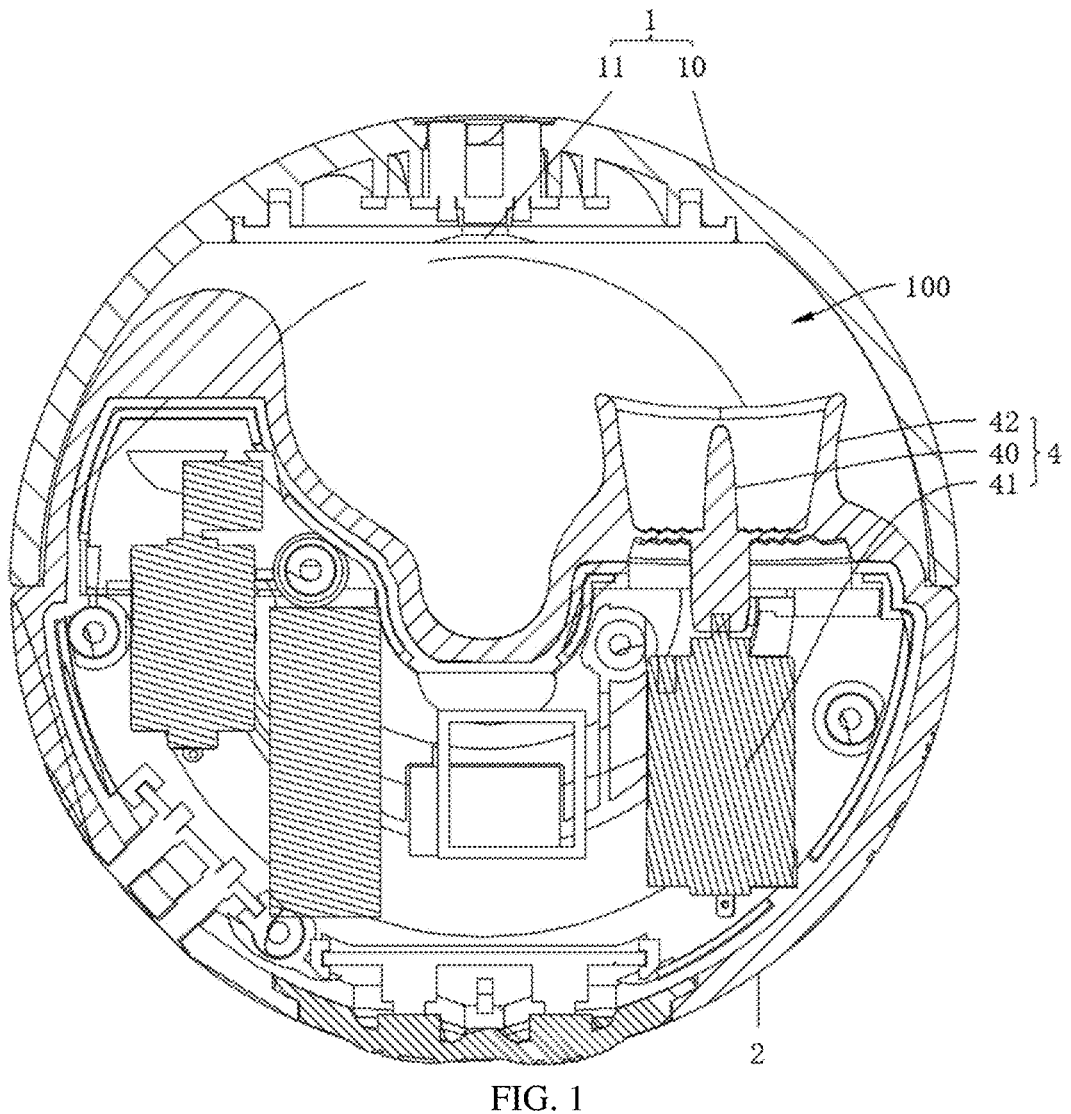
FIG. 1 is a sectional view of an adult toy provided in some embodiments of the present disclosure.
Figure 2:
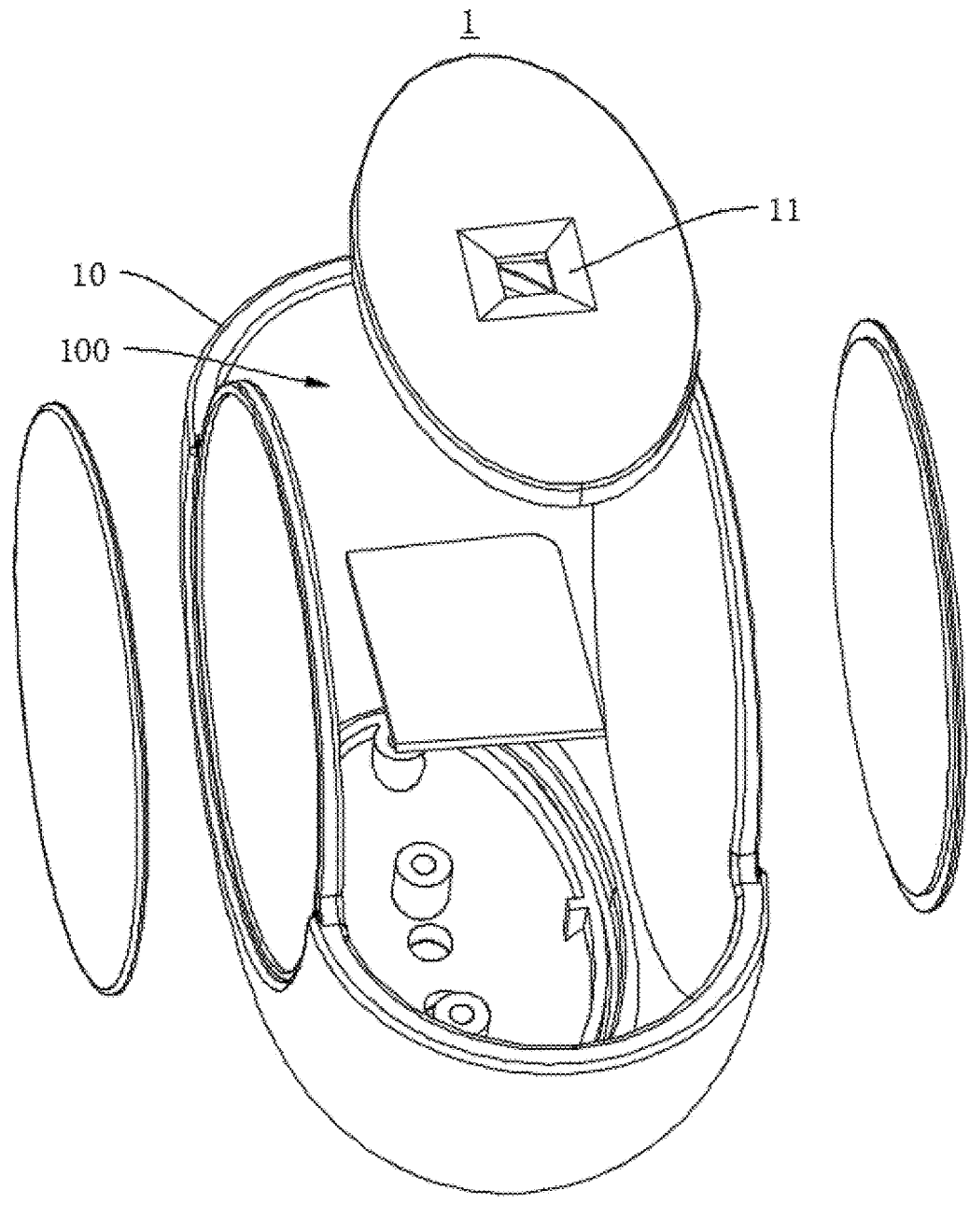
FIG. 2 is an exploded view of a disinfection device provided in some embodiments of the present disclosure.
Figure 3:
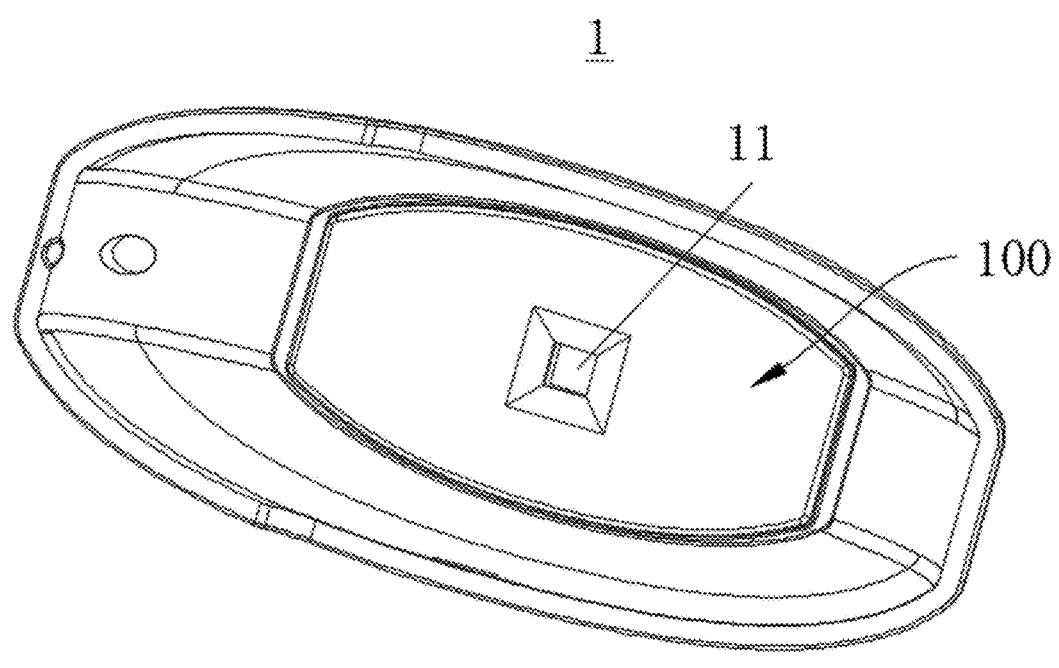
FIG. 3 is a schematic structural diagram of a disinfection device provided in some embodiments of the present disclosure.
Figure 4:
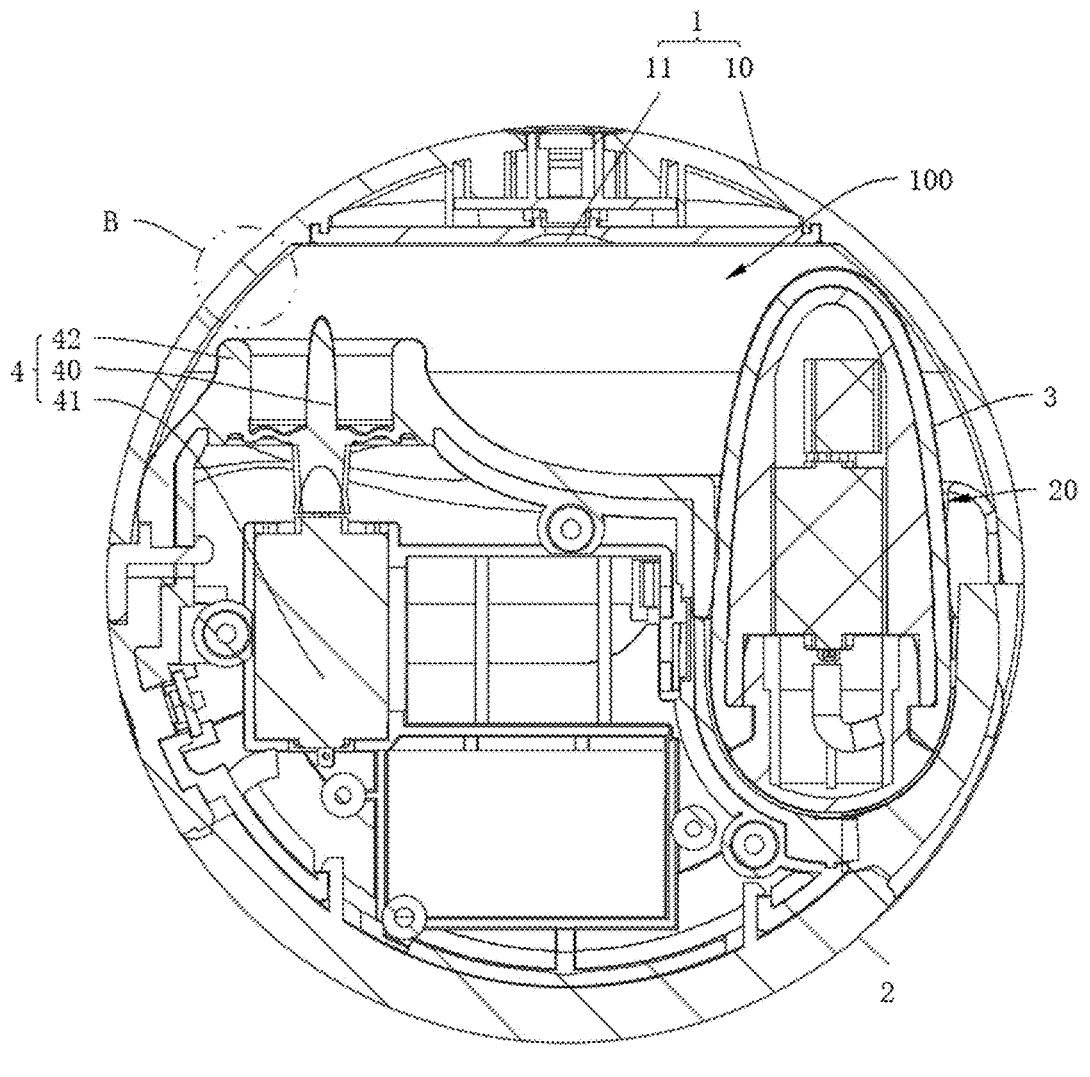
FIG. 4 is a sectional view of an adult toy provided in some other embodiments of the present disclosure.

Reference numerals in the figures: 1—disinfection device; 10—protective shell; 100—disinfection cavity; 1000—spectral reflection layer; 1001—exhaust assembly; 11—disinfection spectrum generation assembly; 12—light guide assembly; 120—incident port; 121—optical path; 122—exit port; 14—first motion platform; 15—light condensing member; 16—light scanning assembly; 17—disinfection indication assembly; 170—light-emitting unit; 2—housing; 20—first connecting portion; 3—vibration massage assembly; 30—second connecting portion; 4—second massage assembly; 40—swinging blade; 41—second driving assembly; and 42—contact ring wall.

DETAILED DESCRIPTIONS OF THE EMBODIMENTS

In order to make the objectives, technical solutions and advantages of the embodiments of the present disclosure clearer, the technical solutions in the embodiments of the present disclosure will be clearly and completely described below in combination with the accompanying drawings in the embodiments of the present disclosure. Apparently, the embodiments described are merely some rather than all of the embodiments of the present disclosure. Based on the embodiments of the present disclosure, all other embodiments acquired by those of ordinary skill in the art without making creative efforts fall within the scope of protection of the present disclosure.

Unless defined otherwise, all technical and scientific terms used herein have the same meanings as commonly understood by those skilled in the art to which the present disclosure belongs. The terms used in the specification of the present disclosure are for the purpose of describing specific embodiments merely and are not intended to limit the present disclosure. The terms "including" and "having", and any variations thereof in the specification, the claims and the above accompanying drawings are intended to cover non-exclusive inclusion. The terms "first", "second" and the like in the specification and the claims or the above accompanying drawings are used to distinguish different objects and are not intended to indicate a specific order or hierarchical relationship.

When the term "embodiment" is referred to herein, it means that specific features, structures or characteristics described in combination with the embodiment are included in at least one embodiment of the present disclosure. When this phrase occurs at various positions in the specification, it neither necessarily refers to the same embodiment, nor refers to an independent or alternative embodiment mutually exclusive to other embodiments. Those skilled in the art understand both explicitly and implicitly that the embodiments described herein can be combined with other embodiments.

In the description of the present disclosure, it is to be noted that, unless otherwise explicitly specified and defined, the terms "mounting", "connected", "connecting" and "attaching" are to be understood in a broad sense, for embodiment, they may be a fixed connection, a detachable connection, or an integrated connection; and may be a direct connection, or an indirect connection via an intermediate medium, or communication inside two elements. For those of ordinary skill in the art, the specific meanings of the above terms in the present disclosure may be understood according to specific circumstances.

The term "and/or" in the present disclosure, which is merely an association relation describing an associated object, means that there maybe exist three relations, for embodiment, A and/or B maybe represent three situations: A exists alone, A and B exist at the same time, and B exists alone. In addition, the character "/" mentioned in the present disclosure generally indicates that the associated objects are in an "or" relationship.

The term "a plurality of" used in the present disclosure refers to two or more (including two), and similarly, "a plurality of groups" refers to two or more groups (including two groups), and "a plurality of sheets" refers to two or more sheets (including two sheets).

According to some embodiments of the present disclosure, optionally, as shown in FIGS. 1-4, the present disclosure provides an adult toy disinfection device 1, and the adult toy disinfection device includes a protective shell 10 with an opening, where an inner cavity of the protective shell 10 is a disinfection cavity 100, and the adult toy disinfection device 1 includes a disinfection spectrum generation assembly 11 and a first driving assembly; at least a portion of the adult toy to be disinfected may be placed in the disinfection cavity 100 through the opening; the first driving assembly is electrically connected to the disinfection spectrum generation assembly 11 and configured to drive the disinfection spectrum generation assembly 11 to generate a disinfection spectrum; and the disinfection spectrum generation assembly 11 is disposed on an inner side of the disinfection cavity 100, such that the disinfection spectrum directly irradiates or indirectly irradiates the space of the disinfection cavity 100 by means of an optical path 121.

The disinfection spectrum refers to light in a specific wavelength range that has bactericidal and disinfection effects. In the adult toy disinfection device 1, the disinfection spectrum includes, but is not limited to, short-wave ultraviolet light, blue light, and other light that may destroy a cell structure of microorganisms. The disinfection principle is that the DNA or RNA molecular structure of microorganisms is destroyed by irradiating the microorganisms (such as bacteria, molds, and the like), resulting in that the microorganisms cannot reproduce or even die, thereby achieving the purpose of killing the microorganisms.

The "indirectly irradiates the space of the disinfection cavity 100 by means of an optical path 121" mentioned in the present disclosure means that after the adult toy is placed in the disinfection cavity 100, when some portions of the adult toy to be disinfected are blocked by the toy structure and cannot be directly irradiated by the disinfection spectrum, the spectrum may be changed in a propagation direction through the optical path 121 (such as reflection, refraction, and other functions of a cavity wall) formed inside the disinfection cavity 100, and indirectly irradiates these portions blocked.

The light and spectrum mentioned in the present disclosure both refer to the disinfection spectrum generated by the disinfection spectrum generation assembly 11.

A sensor (such as a weight sensor, an infrared sensor, and the like) may be arranged in the disinfection cavity 100 to automatically detect whether the adult toy is placed in the disinfection cavity 100 and whether the adult toy is placed properly, and then the first driving assembly automatically drives the activation of the disinfection spectrum generation assembly 11 to disinfect the adult toy properly placed in the disinfection cavity 100.

The disinfection cavity 100 may be provided with a drying system, and after disinfection, gentle warm air or low-humidity air is automatically blown to dry the adult toy. A humid environment is a breeding ground for microbial growth, and drying may further improve the disinfection effect and prevent secondary growth of molds during storage.

After using the adult toy, the user simply rinses a surface of the adult toy to remove obvious residues, and then places a portion of the adult toy to be disinfected (usually the portion in contact with the user's body) into the disinfection cavity 100 of the device through the opening. The disinfection spectrum generation assembly 11 starts working and generates light with strong bactericidal and disinfection effects, and the light directly irradiates or indirectly irradiates an inner space of the disinfection cavity 100 and a surface of the adult toy, to efficiently kill bacteria, viruses, molds, and other microorganisms in the residues such as skin secretions and sweat on the surface of the adult toy. The adult toy disinfection device 1 provided by the present disclosure, by utilizing the strong bactericidal capability of specific spectra, is capable of thoroughly killing various pathogenic microorganisms (such as bacteria, viruses, mold spores, and the like) attached to the surface of the adult toy, which solves the problem that microbial residues cannot be completely removed through manual cleaning, and reduces the risks of microbial growth, product contamination, and cross-infection caused by incomplete cleaning. The user only needs to simply place the adult toy and start the disinfection device 1 provided by the present disclosure, without need of cumbersome manual scrubbing, wiping, and worry about incomplete rinsing. High automation significantly reduces the cleaning burden and enhances the user convenience and pleasure. Compared with chemical disinfection methods such as alcohol wiping, physical disinfection with light of specific wavelengths does not cause adverse effects such as corrosion, dissolution, aging, or texture change of common adult toy materials such as silicone, a thermoplastic elastomer (TPE), and Acrylonitrile Butadiene Styrene (ABS) plastic, thereby ensuring the service life and safety of the adult toy.

Figure 5:
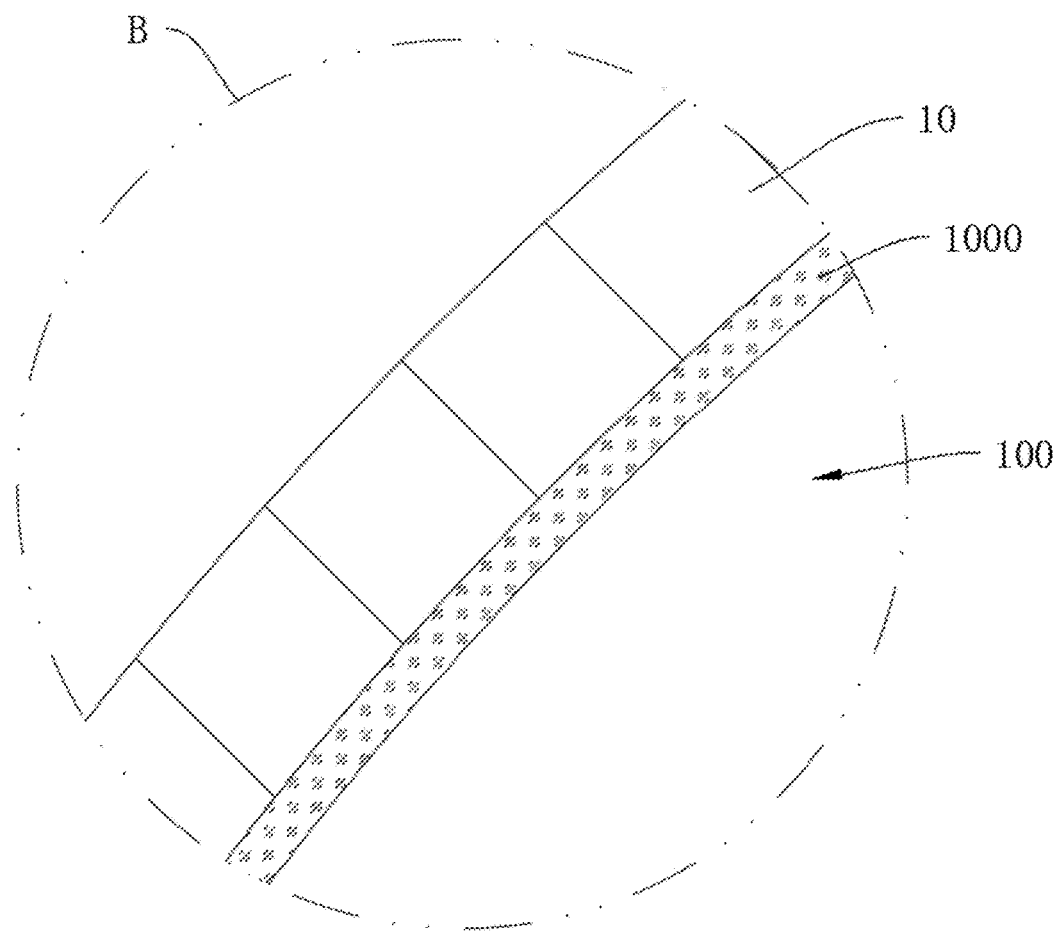
FIG. 5 is an enlarged view of a portion B in FIG. 3.

According to some embodiments of the present disclosure, optionally, as shown in FIG. 5, the disinfection cavity 100 is provided with a spectral reflection layer 1000; and the spectral reflection layer 1000 is disposed on an inner surface of the disinfection cavity 100 and configured to reflect the disinfection spectrum.

The spectral reflection layer 1000 has a very high reflectivity for the disinfection spectrum.

The spectral reflection layer 1000 may include, but is not limited to, a high-purity aluminum reflective mirror surface, a special ultraviolet-C (UVC) high-reflection coating/film, a sintered magnesium fluoride ($MgF_2$) or calcium fluoride ($CaF_2$) coating, and the like.

A cleaning device may be arranged in the disinfection cavity 100, such that dust and particles attached to the surface of the spectral reflection layer 1000 may be removed by means of electrostatic dust removal, and the like.

During the disinfection of the adult toy, the disinfection spectrum generation assembly 11 generates a disinfection spectrum, part of the disinfection spectrum directly irradiates the surface of the adult toy, and the remaining part of the disinfection spectrum irradiates the inner surface of the disinfection cavity 100. Since the inner surface of the disinfection cavity is covered with the spectral reflection layer 1000, the remaining part of the disinfection spectrum is efficiently reflected back, and the reflected disinfection spectrum irradiates the inner space of the cavity and the surface of the adult toy again. This process will occur repeatedly (light "bounces" between reflection layers) until the energy is absorbed or attenuated. As a result, portions of the adult toy originally in shadow areas not directly irradiated by the light (such as a recessed portion of the adult toy, and an interior of the gap) are irradiated by the light reflected for many times, thereby reducing dead zones of disinfection. The spectral reflection layer 1000 reduces the ineffective absorption and loss of light on the cavity wall, and limits more light energy in the cavity and guides the same to the surface of the adult toy to be disinfected. Equivalently, an effective light dose is increased, thereby improving the microbial killing rate and achieving the more thorough disinfection effect within the same time.

According to some embodiments of the present disclosure, optionally, the spectral reflection layer 1000 has a diffuse reflection structure configured to achieve diffuse reflection of the disinfection spectrum that irradiates the inner surface of the disinfection cavity 100.

The diffuse reflection structure is a roughened surface on a micro scale obtained by means of sandblasting, etching, embossing, and other treatments on a substrate of the spectral reflection layer 1000, or the diffuse reflection surface is formed by particles generated by coating curing after applying a specialized coating containing high-reflectivity particles (such as high-purity alumina powder, barium sulfate powder, or specially formulated titanium dioxide powder, where these materials need to have high reflectivity and stability for the disinfection spectrum) on the substrate of the spectral reflection layer 1000.

Diffuse reflection structures with different diffuse reflection characteristics may be applied for different areas on the surface of the disinfection cavity 100. For embodiment, a strong scattering (wide-angle) diffuse reflection structure is applied to deep grooves or entrances, which facilitates light introduction, a diffuse reflection structure with extremely high reflectivity but a slightly narrow scattering angle is applied to open areas to maintain high light intensity, and a diffuse reflection structure with certain directional diffuse reflection characteristics is used near the disinfection spectrum generation assembly 11 to guide more light to distal dead zones. This design enables to more intelligently distribute light energy and strengthen the irradiation of weak areas in a targeted manner.

When the disinfection spectrum irradiates the spectral reflection layer 1000 with the diffuse reflection structure, the light scatters in all directions (at all angles), and diffusely reflected light fills the entire disinfection cavity 100 to form a highly uniform and non-directional light field environment, and the scattered light from all directions irradiates all exposed surfaces of the adult toy, such that all surfaces of the adult toy receive sufficient and similar disinfection doses. The scattered light easily bypasses obstacles and penetrates into recessed portions, holes, thread gaps, and shadow areas formed due to self-occlusion by the adult toy, that are hardly exposed to direct light, thereby further reducing the dead zones of disinfection. Additionally, when the scattered light encounters any other cavity wall or the surface of the adult toy, the light will undergo diffuse reflection again, and this process continues until the energy is attenuated. The superposition of multiple diffuse reflections further enhances the uniformity of the light field and the capability to cover dead zones.

Figure 6:
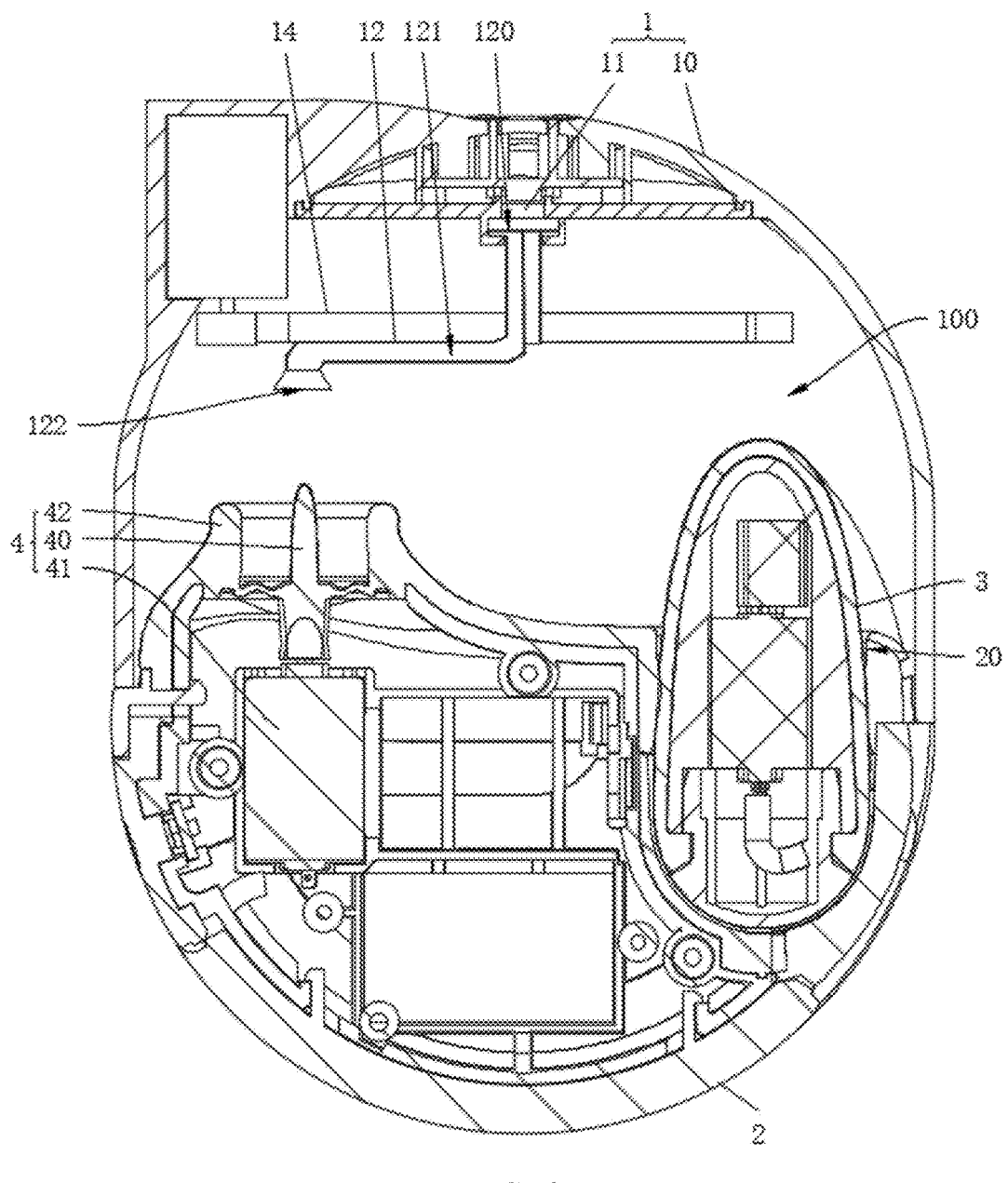
FIG. 6 is a sectional view of an adult toy provided in still other embodiments of the present disclosure.

According to some embodiments of the present disclosure, optionally, as shown in FIG. 6, the device further includes a light guide assembly 12 including an incident port 120, an optical path 121, and an exit port 122; the light guide assembly 12 is disposed in the disinfection cavity 100, and the incident port 120 is disposed at the disinfection spectrum generation assembly 11; one or more exit ports 122 are disposed at one or more key disinfection portions of the adult toy; and the optical path 121 is configured to guide the disinfection spectrum incident from the incident port 120 to the exit port 122 for emission.

A material of the optical path 121 of the light guide assembly 12 has the characteristics of high transmittance, high reflectivity, and low loss for the disinfection spectrum.

The material of the optical path 121 includes, but is not limited to, quartz (fused quartz), zirconium fluoride, aluminum fluoride, and the like.

The shape of the exit port 122 is adapted to the shape of a corresponding target area of the adult toy, and for embodiment, a circular port corresponds to a circular hole, and a flat port corresponds to a gap.

The number of the exit ports 122 is not less than the number of the key disinfection portions, and each of the key disinfection portions is directly opposite to at least one of the exit ports 122.

After the adult toy is placed in the disinfection cavity 100, the key disinfection portions are aligned with the exit ports 122 of the light guide assembly 12, the disinfection spectrum generation assembly 11 starts working to generate a disinfection spectrum, part of the disinfection spectrum directly irradiates or indirectly irradiates an outer surface of the adult toy, and the remaining part of the disinfection spectrum enters the incident port 120 of the light guide assembly 12; and the light entering the light guide assembly 12 is transmitted through the optical path 121 in a guided manner and finally emitted from one or more exit ports 122 of the light guide assembly 12, the exit ports 122 are pre-designed to be aligned with the key disinfection portions of the adult toy, the light directly, closely and intensively irradiates the key disinfection portions, and the light guide assembly 12 actively delivers and injects the disinfection spectrum into the shadow areas, which reduces the dead zones of disinfection, and achieves deep disinfection. Through the light guide assembly 12, the disinfection spectrum accurately hits the target, prevents energy waste in non-target areas, and enhances the thoroughness and reliability of disinfection of the key disinfection portions. Precisely targeting the portions most difficult to be disinfected prevents long-time and high-intensity excessive irradiation of the entire adult toy performed to ensure the safety of the portions, thereby shortening the overall disinfection time or reducing the power of the disinfection spectrum generation assembly 11.

According to some embodiments of the present disclosure, optionally, as shown in FIG. 6, the device further includes a first motion platform 14 carrying the light guide assembly 12 for motion.

The material of the first motion platform 14 includes, but is not limited to, carbon fiber, high-strength engineering plastic, and the like, which reduces a weight and inertia of the first motion platform 14, thereby improving a response speed and energy efficiency.

The first motion platform 14 may only drive the exit port 122 of the light guide assembly 12 to move.

One (or a few) exit port 122 of the light guide assembly 12, driven by the first motion platform 14, efficiently and sequentially covers a plurality of key disinfection portions at different positions of the adult toy. There is no need to separately design fixed exit ports 122 for each portion, which simplifies the structure, reduces costs, and improves versatility. When any adult toy is placed in the cavity in any manner, the first motion platform 14 adjusts a position and angle of the exit port 122 of the light guide assembly 12 to find and accurately irradiate the key disinfection portions, thereby adapting to adult toys of different shapes at any positions and angles.

According to some embodiments of the present disclosure, optionally, the first driving assembly has a first disinfection driving strategy; the first disinfection driving strategy includes a first driving program implemented by software and/or hardware circuits; and the first driving program is configured to drive a plurality of the disinfection spectrum generation assemblies 11 corresponding to a plurality of the key disinfection portions to light up one by one.

The first disinfection strategy is implemented by a timer chip, a logic circuit, and a microcontroller in combination with other software.

Voltage drop (also known as the voltage loss) refers to a voltage difference generated at both ends of a conductor due to a resistance of the conductor when current flows through the conductor (such as a wire). In simple terms, when a power supply outputs a certain voltage, current flows from a positive terminal of the power supply to an electrical device (such as the disinfection spectrum generation assembly 11) through the wire, and part of the electrical energy is consumed due to the resistance of the wire, such that an actual voltage obtained by the electrical device is lower than an initial voltage output by the power supply, where this difference is the voltage drop.

A plurality of the disinfection spectrum generation assemblies 11 corresponding to a plurality of the key disinfection portions are generally connected to the power supply through the same wire, and when a plurality of high-power assemblies (i.e., the disinfection spectrum generation assemblies 11) are lit up simultaneously, total working current is extremely large. A larger current I indicates a greater voltage drop (voltage loss) caused by a resistance R of the wire, which results in that an actual working voltage of the assembly away from the power supply is significantly lower than a nominal value. The strategy of lighting up the disinfection spectrum generation assemblies 11 one by one ensures that only a single disinfection spectrum generation assembly 11 works at any time, thereby significantly reducing the working current I (only the working current of a single disinfection spectrum generation assembly 11). Therefore, the voltage drop on the wire is reduced, and even when a longer or thinner wire is used, it is ensured that each assembly obtains a stable working voltage close to the voltage of the power supply during operation. An output wavelength of the disinfection spectrum generation assembly 11 is extremely sensitive to the working voltage. Minor fluctuations in the voltage (caused by the line loss or power supply fluctuations) cause wavelength shifts, and the strategy of lighting up the disinfection spectrum generation assemblies 11 one by one provided by the present disclosure ensures that each of the disinfection spectrum generation assemblies 11 works at a stable optimal voltage during the working period, and outputs an accurate and stable target disinfection spectrum, thereby ensuring the highest disinfection efficiency.

Figure 7:
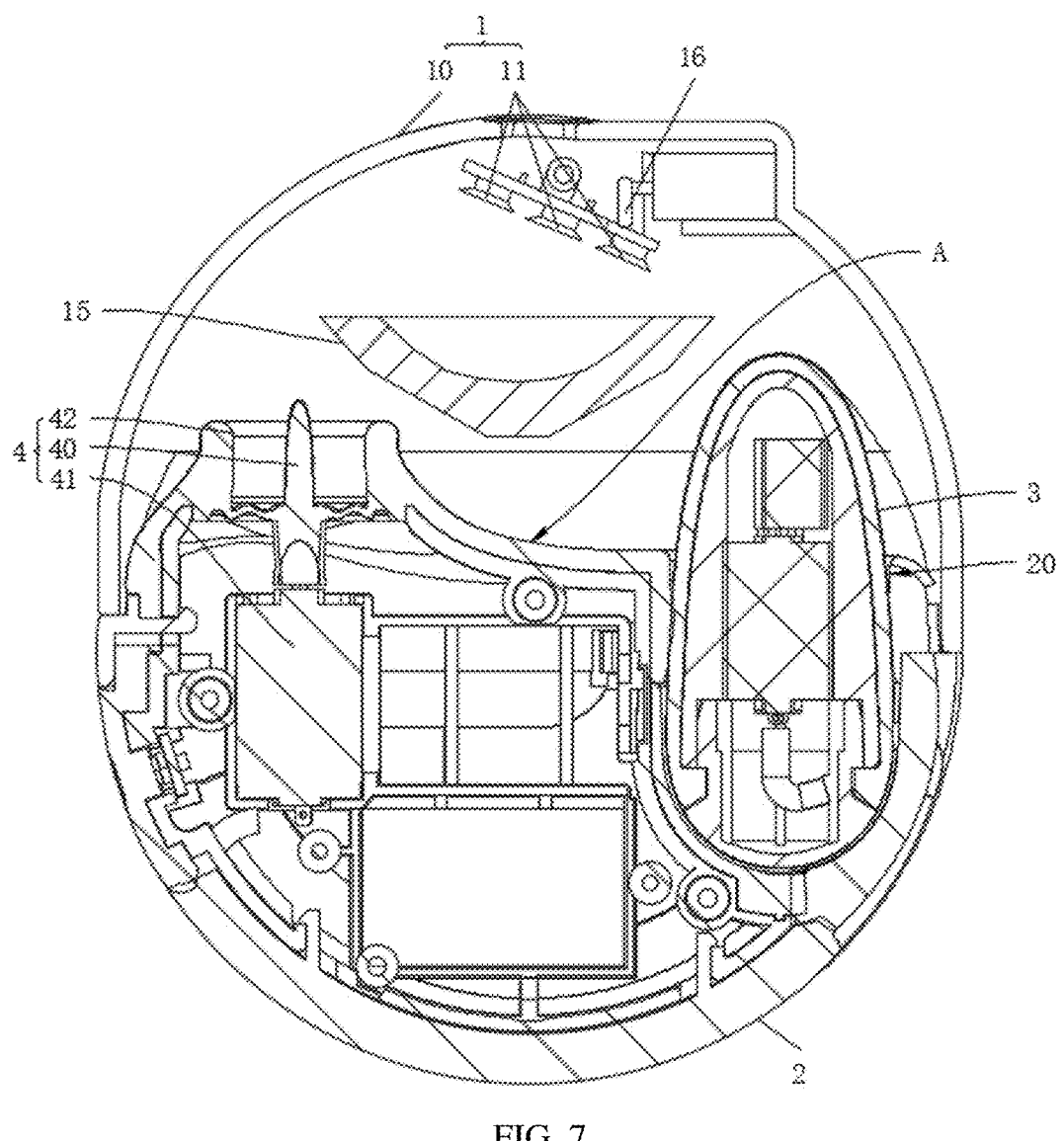
FIG. 7 is a sectional view of an adult toy provided in further embodiments of the present disclosure

According to some embodiments of the present disclosure, optionally, as shown in FIG. 7, the device further includes a light condensing member 15 and a light scanning assembly 16; the disinfection spectrum forms a focused light spot through the light condensing member 15, and the light scanning assembly 16 is configured to cause the focused light spot of the disinfection spectrum to perform scanning motion in an area A; and the area A covers an area of the adult toy to be disinfected.

The area A mentioned in the present disclosure is a plane A shown in the figure.

A material of the light condensing member 15 has high transmittance or high reflectivity for the disinfection spectrum. The material of the light condensing member 15 includes, but is not limited to, fused quartz, a high-purity aluminum coating, and the like.

When the disinfection spectrum generation assembly 11 works, the generated disinfection spectrum first passes through the light condensing member 15, the light condensing member 15 converges the originally divergent light to form a focused light spot with a significantly higher energy density and smaller size, and the light scanning assembly 16 drives the high-energy focused light spot to perform fast and controllable motion (i.e., scanning) in the pre-defined or intelligently recognized area A. The area A is designed to cover the entire portion of the adult toy to be disinfected in the disinfection cavity 100. The disinfection device 1 provided by the present disclosure concentrates the limited light source energy on an extremely small area through the light condensing member 15, such that the energy density (light power per unit area) at the light spot is increased, thereby improving the disinfection effect on the irradiated area. Since energy is highly concentrated on the points that need to be disinfected and is not evenly dispersed, an overall energy utilization rate of the disinfection spectrum is improved. Additionally, although the energy at the light spot is relatively high, the light scanning assembly 16 causes the light spot to dwell at a single point for a short time, resulting in that the heat does not accumulate significantly before the light spot moves away. Therefore, even when a higher-power light source is used, the risk of overheating, melting or accelerated photoaging of the surface of the adult toy caused by long-time irradiation is effectively prevented.

According to some embodiments of the present disclosure, optionally, as shown in FIG. 7, a plurality of the disinfection spectrum generation assemblies 11 are arranged; and the plurality of the disinfection spectrum generation assemblies 11 form a focused light spot through the same light condensing member 15.

The disinfection spectra emitted by the plurality of the disinfection spectrum generation assemblies 11 have different peak wavelengths, such that the converged spectrum covers a wider effective disinfection band, which is potentially effective for a wider range of microbial species and reduces the risk that some microorganisms develop tolerance to a single wavelength.

The power of a single disinfection spectrum generation assembly 11 is limited, an energy density of the focused light spot has an upper limit, and when the light energy of the plurality of the disinfection spectrum generation assemblies 11 is converged onto the same tiny light spot through a same optical system, a peak energy density (light power per unit area) of the light spot is multiplied, and the light spot has stronger instantaneous disinfection capability. Higher energy density means that the dwell time of the light spot required to achieve the same disinfection dose is shorter, or a coverage frequency in the same time is increased, which speeds up the overall disinfection. Additionally, a plurality of small light sources are converged by the same light condensing member 15 to form a light spot with a size equivalent to or even smaller than that focused by a single light source, which prevents the problem of light spot enlargement and limited energy density increase caused by simply increasing the power of the light source, and ensures that the light spot with the strong disinfection capability accurately acts on various small structures on the surface of the adult toy.

According to some embodiments of the present disclosure, optionally, as shown in FIG. 7, the light scanning assembly 16 is a second motion platform carrying the disinfection spectrum generation assembly 11 for motion.

A motion speed of the second motion platform may be set according to an energy density of the focused light spot and a degree of microbial contamination of the portion to be disinfected, that is, the motion speed may be reduced for seriously contaminated areas to prolong the irradiation time, and the motion speed may be increased in clean areas to reduce redundant energy consumption.

The second motion platform, as the light scanning assembly 16, drives the disinfection spectrum generation assembly 11 to move in the disinfection cavity 100 according to a predetermined trajectory. Since the light condensing member 15 is relatively fixed to the disinfection spectrum generation assembly, when the platform moves, the focused light spot emitted by the light condensing member 15 changes in an irradiation point with the positional change of the disinfection spectrum generation assembly, thereby completing the scanning motion in the area A and achieving full coverage of the portions of the adult toy to be disinfected.

Figure 8:
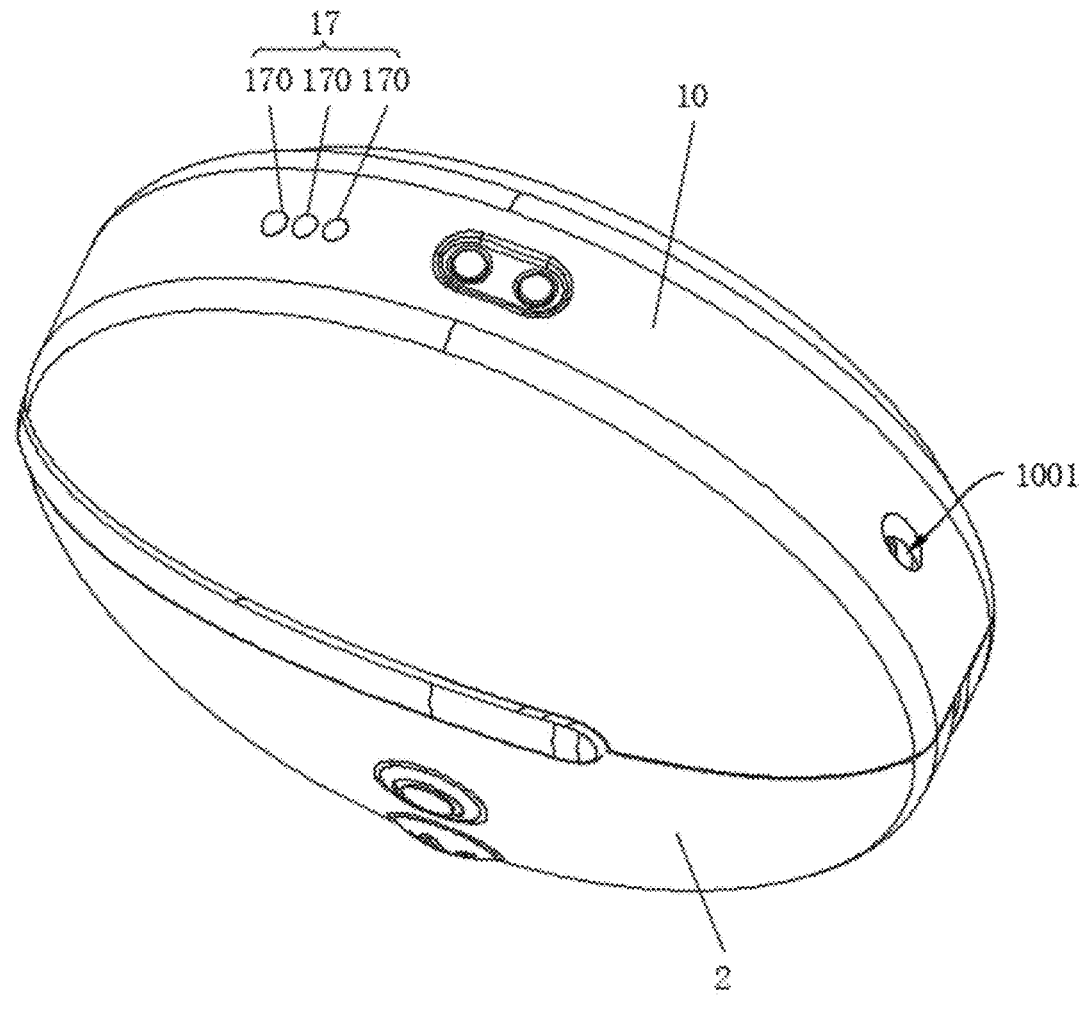
FIG. 8 is a schematic diagram of an external structure of an adult toy provided in some embodiments of the present disclosure.
Figure 9:
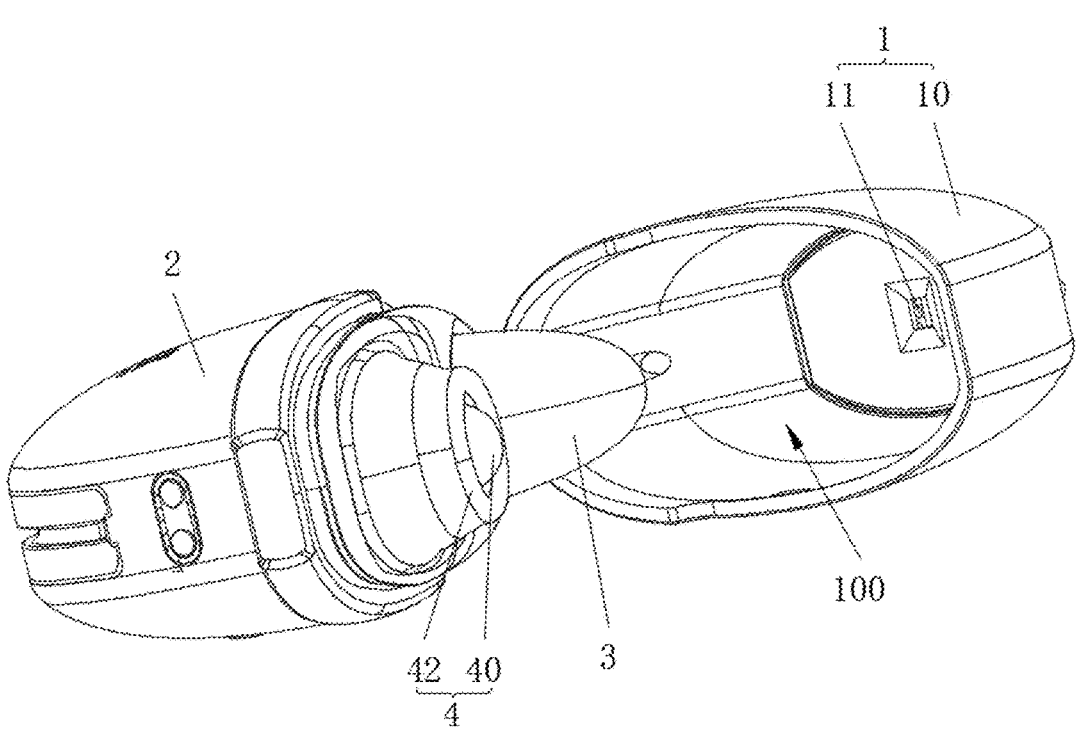
FIG. 9 is a schematic structural diagram when a vibration massage assembly is detached from a housing provided in some embodiments of the present disclosure.

According to some embodiments of the present disclosure, optionally, as shown in FIG. 8, the disinfection cavity 100 includes an exhaust assembly 1001; and water vapor inside the disinfection cavity 100 is discharged outside the disinfection cavity 100 through the exhaust assembly 1001.

The disinfection cavity 100 may be further provided with a heating assembly, and evaporation of water vapor is first accelerated through heating, and then the water vapor is discharged by the exhaust assembly 1001, which forms an efficient drying process.

The exhaust assembly 1001 includes, but is not limited to, an exhaust port disposed on the protective shell 10.

When the exhaust assembly 1001 is an exhaust port, a filter mesh may be arranged inside therein to prevent external dust and impurities from entering the disinfection cavity 100.

The adult toy may be simply cleaned before being placed into the disinfection cavity 100, and residual water on the surface of the adult toy may remain inside the cavity, which will form a humid environment and a new breeding ground for the growth of bacteria and molds, such that even after disinfection, microorganisms reproduce again due to humidity. The exhaust assembly 1001 timely discharges the water vapor formed after water volatilization, to keep the cavity dry, eliminate the risk of secondary contamination caused by humidity, and consolidate the disinfection effect. Furthermore, a humid environment affects the performance of electronic elements and mechanical structures such as the disinfection spectrum generation assembly 11 (e.g., causing short circuits and rusting of metal components), and the exhaust assembly 1001 prolongs the service life of each assembly of the device and reduces the probability of failure by maintaining the dryness of the cavity.

According to some embodiments of the present disclosure, optionally, as shown in FIG. 8, the device further includes a disinfection indication assembly 17; the disinfection indication assembly 17 includes a light-emitting unit 170; and the light-emitting unit 170 is in an operating state during the disinfection process.

The light-emitting unit 170 may cooperate with a buzzer to provide both visual and auditory prompts for the user, which is suitable for noisy environments or users with poor eyesight.

On the one hand, the operating state of the light-emitting unit 170 enables the user to quickly know that the disinfection device 1 is working, which prevents accidental shutdown or premature removal of the adult toy and ensures the complete execution of the disinfection process; and on the other hand, during the disinfection process, the operating state of the light-emitting unit 170 indirectly reminds the user of high energy inside the disinfection device 1, which prevents the user from opening the cavity and be exposed to the disinfection spectrum in this case, thereby reducing the risk of accidental injury.

According to some embodiments of the present disclosure, optionally, the operating state is one or more of breathing flash, color gradient flash, and chasing light flash.

Compared with single continuous illumination or regular flashing, the above three illumination modes have higher visual distinctiveness, thereby making it easier to attract the user's attention and play a prompting role. Different illumination modes correspond to different disinfection stages or enable to distinguish the working states of different spectra, thereby achieving more meticulous information transmission for the user.

According to some embodiments of the present disclosure, optionally, as shown in FIGS. 1-4 and 8-9, the present disclosure provides an adult toy, and the adult toy includes a housing 2, a battery, and a control circuit, further including a disinfection device 1, a vibration massage assembly 3, and a second massage assembly 4; the battery, the control circuit, and the massage assemblies are electrically connected; the disinfection device 1 includes a disinfection spectrum generation assembly 11, a first driving assembly, and a protective shell 10 with an opening, where an inner cavity of the protective shell 10 is a disinfection cavity 100; the vibration massage assembly 3 and the second massage assembly 4 may be placed in the disinfection cavity 100 through the opening, and the housing 2 and the protective shell 10 may be combined to form an enclosed cavity; and the disinfection spectrum generation assembly 11 is disposed on an inner side of the disinfection cavity 100, and the first driving assembly is configured to drive the disinfection spectrum generation assembly 11 to generate a disinfection spectrum irradiating the space of the disinfection cavity 100.

The protective shell 10 and an outer shell may be combined into a complete circular housing 2.

A sealing member such as a silicone sealing ring may be arranged at a joint between the housing 2 and the protective shell 10 to enhance the effect of sealing therebetween, thereby ensuring that the enclosed cavity is light-tight and dustproof, and preventing external impurities from entering during the disinfection process.

After using the vibration massage assembly 3 and the second massage assembly 4 of the adult toy provided by the present disclosure, the user resets the vibration massage assembly 3 and the second massage assembly 4 from the working position, then places them into the disinfection cavity 100 through the opening, and pushes the housing 2 and the protective shell 10 together to form the enclosed cavity. After the disinfection function is activated, the first driving assembly drives the disinfection spectrum generation assembly 11 to generate a disinfection spectrum, the disinfection spectrum irradiates the enclosed space of the disinfection cavity 100 to disinfect the surfaces of the vibration massage assembly 3 and the second massage assembly 4, and after completion of the disinfection process, a power supply of the first driving assembly is disconnected, and the housing 2 and the protective shell 10 protect the vibration massage assembly 3 and the second massage assembly 4 until the user uses them next time. The adult toy provided by the present disclosure integrates the disinfection device 1 and the massage assemblies, and the adult toy is directly disinfected after use for storage, which eliminates the cumbersome process of separately cleaning and disinfecting the adult toy after massage, and enhances the use convenience of the adult toy. The enclosed cavity formed by the combination of the housing 2 and the protective shell 10 not only prevents the leakage of the disinfection spectrum (thereby protecting the user), but also ensures that the disinfection spectrum reflects and circulates in the enclosed cavity, thereby enhancing the disinfection coverage of the surfaces and gaps of the vibration massage assembly 3 and the second massage assembly 4, and achieving more thorough disinfection than that in an open environment. The vibration massage assembly 3 and the second massage assembly 4 may be directly stored in the enclosed cavity formed by the combination of the housing 2 and the protective shell 10, which prevents the scattering or loss of assemblies, and facilitates storage and carrying due to an overall compact structure.

Figure 11:
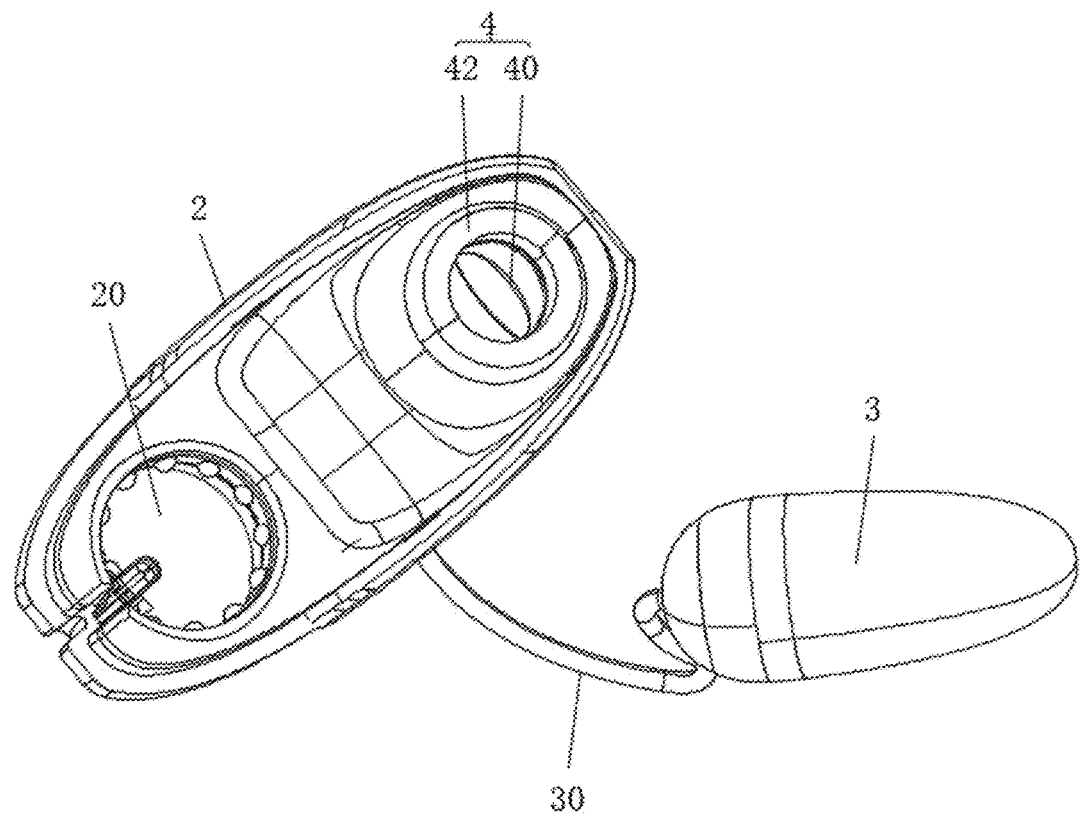
FIG. 11 is a schematic structural diagram when a vibration massage assembly is detached from a housing provided in some other embodiments of the present disclosure.
Figure 12:
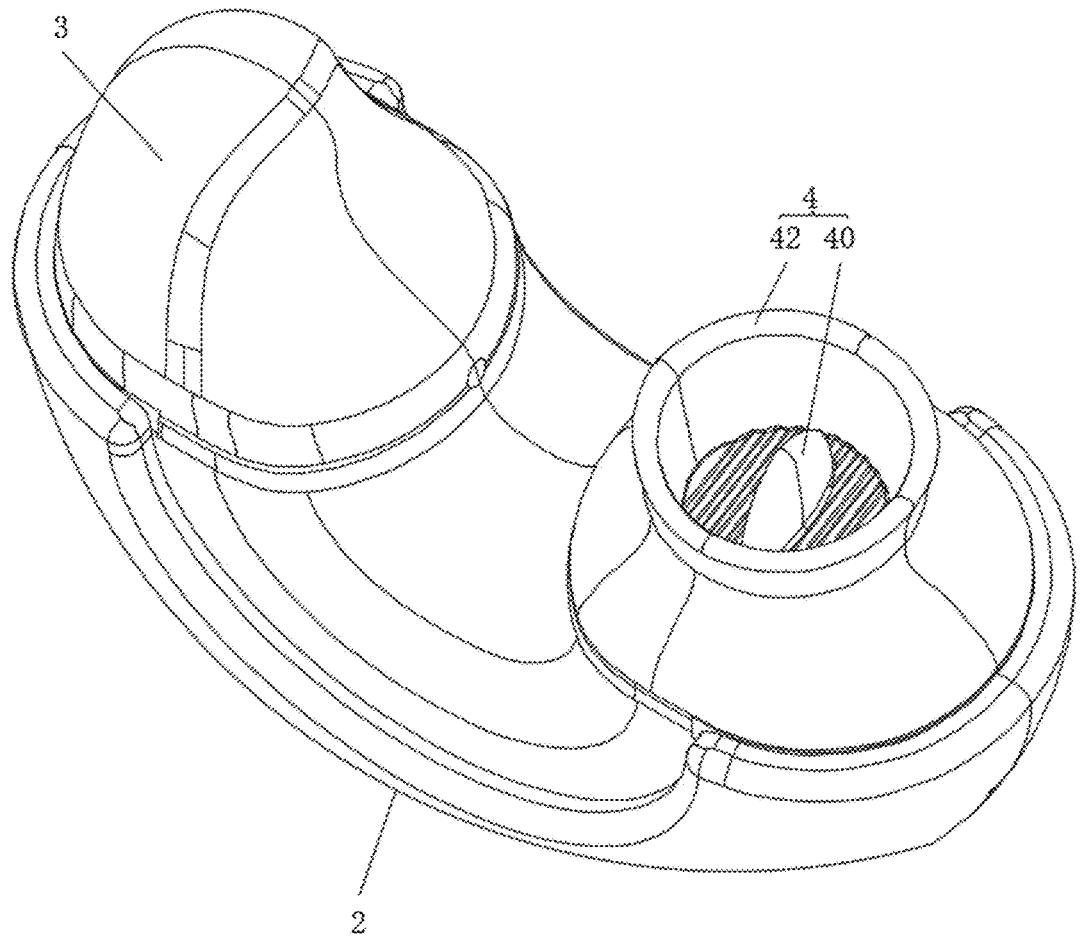
FIG. 12 is a schematic structural diagram of a housing and a second massage assembly provided in some embodiments of the present disclosure.

According to some embodiments of the present disclosure, optionally, as shown in FIGS. 7 and 11, the housing 2 includes a first connecting portion 20; and the vibration massage assembly 3 is detachably connected to the housing 2 through the first connecting portion 20.

The first connecting portion 20 includes, but is not limited to, a snap-fit clasp, a threaded interface, a magnetic attraction device, a plug-in interface, or the like.

The vibration massage assembly 3 needs to be in close contact with the human body during use, and after being disassembled from the housing 2, the vibration massage assembly 3 may be flexibly inserted into private spaces such as vagina and rectum due to a smaller size, to directly act on sensitive areas in the body. Compared with the design of integration with the housing 2, the assembly disassembled better fits a curve of an internal physiological structure, and achieves more precise touch of target points during massage, thereby enhancing the pertinence and comfort of massage, and meeting the needs of internal massage.

Figure 10:
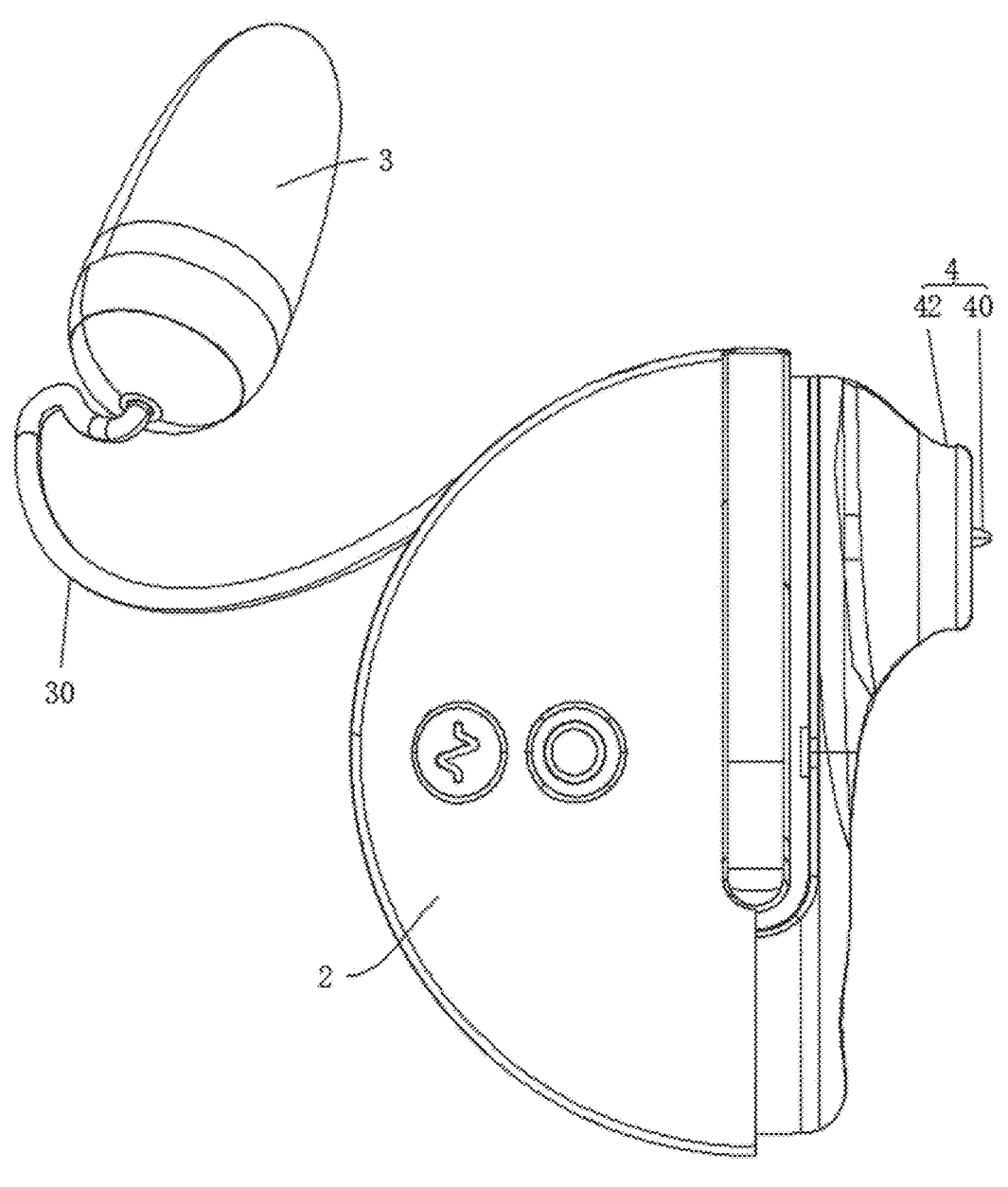
FIG. 10 is a schematic structural diagram when a housing is detached from a protective shell of an adult toy provided in some embodiments of the present disclosure.

According to some embodiments of the present disclosure, optionally, as shown in FIGS. 10-11, the vibration massage assembly 3 includes a second connecting portion 30; and the second connecting portion 30 flexibly connects the vibration massage assembly 3 to the housing 2, and the vibration massage assembly 3 may be pulled through the second connecting portion 30.

The second connecting portion 30 may be of a telescopic structure (such as a retractable silicone rope similar to a tape measure), and the user adjusts a length of the telescopic structure according to the body shape or target area (e.g., lengthening for deeper insertion into the vagina, and shortening for shallow massaging).

The second connecting portion 30 directly or indirectly touches the human body (e.g., potentially touching the skin when pulling), and may be made of a non-toxic and non-irritating material such as medical-grade silicone or a food-grade elastomer to prevent allergic reactions or infections of the user caused by material issues.

In actual use, when the user disassembles the vibration massage assembly 3 from the housing 2, the second connecting portion 30 remains flexibly connected to the vibration massage assembly 3, then the disassembled vibration massage assembly 3 is slowly placed into the target area such as the vagina or rectum, and in this process, an angle of insertion of the vibration massage assembly 3 is adjusted by gently pulling the second connecting portion 30. During massage, when a positional shift is felt, the vibration massage assembly 3 is pulled through the second connecting portion 30 to fine-tune the position of the vibration massage assembly 3. After the massage, the vibration massage assembly 3 is slowly removed from the body through the second connecting portion 30, to prevent discomfort caused by directly pulling out the vibration massage assembly 3. Then the vibration massage assembly 3 is placed into the disinfection cavity 100, and the housing 2 and the protective shell 10 are combined for disinfection. The pulling operation is not complex, and is completed only by holding the housing 2 and pulling the second connecting portion 30, which addresses the inconvenience of adjusting the position of the vibration massage assembly 3 in the body. During the whole massage process, the vibration massage assembly 3 is always connected to the housing 2 through the second connecting portion 30, which prevents the risk of hardly taking out the vibration massage assembly 3 in the human body due to deep insertion, thereby enhancing the safety of use.

According to some embodiments of the present disclosure, optionally, as shown in FIGS. 10-11, the second connecting portion 30 includes a wire; and the wire is configured to electrically connect the vibration massage assembly 3 to the control circuit.

An outer side of the wire may be coated with a skin-friendly waterproof layer (such as silicone and the like) to prevent body fluids from penetrating into the wire core so as to prolong the service life of the wire.

A wire storage slot may be disposed in the housing 2, and the wire is automatically retracted into the slot when not in use, which prevents the wire being exposed, tangled, or knotted, thereby achieving neater storage.

The wire achieves both electrical connection and flexible pulling functions, prevents a dual structure of integrating a separate wire and an independent pulling rope, reduces connecting components between the vibration massage assembly 3 and the housing 2, reduces the risk of entanglement, and simplifies the operation. The direct connection through the wire ensures continuous stability of the power supply and control signals during movement and position adjustment of the vibration massage assembly 3, and prevents sudden power outage or mode switching, thereby enhancing the use reliability.

According to some embodiments of the present disclosure, optionally, as shown in FIGS. 10-11, the vibration massage assembly 3 is of an insertable egg-shaped vibrator structure.

A head of the egg-shaped vibrator may be detachable, and the heads of different shapes (e.g., spherical, pointed) or materials (e.g., thermally conductive silicone, cooling-enhanced metal) may be replaced to meet different sensitivity requirements, which facilitates separate disinfection.

A compact shape of the insertable egg-shaped vibrator adapts well to an internal space of human body, compared with other massage structures, the insertable egg-shaped vibrator facilitates deeper insertion without foreign body sensation, and a vibration source is close to a sensitive area, which reduces energy loss, achieves the more concentrated massage effect, and solves the problem of discomfort when a large assembly is inserted into the body. Additionally, a surface of the egg-shaped vibrator structure is smooth without dead zones, and after the egg-shaped vibrator is placed into the disinfection cavity 100, the spectrum uniformly irradiates curved surfaces and gaps, which ensures the safety for the next use.

According to some embodiments of the present disclosure, optionally, as shown in FIGS. 4, 6-7, and 11, the first connecting portion 20 is a cavity with a single open end, and the vibration massage assembly 3 is connected to the housing 2 in a way of being inserted into the cavity; and after the vibration massage assembly 3 is inserted into the cavity, a massage portion of the vibration massage assembly 3 protrudes from the cavity and achieves a massage function.

A magnet may be embedded at a bottom of the cavity, an iron sheet may be disposed at a corresponding position of the vibration massage assembly 3, and when the vibration massage assembly is inserted, the alignment is assisted by means of a magnetic force, and a fitting degree is enhanced, which facilitates insertion and removal.

The first connecting portion 20 is a cavity with a single open end, and the exposed massage portion retains the full functionality after the vibration massage assembly is inserted into the cavity, such that the vibration massage assembly 3 massages the user's body in the state of being inserted into the cavity. The cavity with the single open end achieves connection through the embedded fitting of the vibration massage assembly 3, and during vibration, a friction between the vibration massage assembly 3 and an inner wall of the cavity offsets a vibration impact force, which reduces the risk of loosening; and additionally, disassembly operations are not complex, but are simple, practical, and convenient, and direct insertion and removal are allowed.

According to some embodiments of the present disclosure, optionally, as shown in FIGS. 1, 4, 5-7, and 10-12, the second massage assembly 4 is fixedly connected to the housing 2, and the second massage assembly 4 includes a swinging blade 40 and a second driving assembly 41; and the second driving assembly 41 drives the swinging blade 40 to swing to massage the user's massage area.

A heating sheet may be disposed in the swinging blade 40, and the swinging blade 40 may be heated to a temperature close to an oral temperature of human, which achieves warm massage for the user by simulating the feeling of real tongue licking, and enhances the massage stimulation to sensitive areas such as the clitoris.

The swinging blade 40 is designed as a small-volume structure shaped like a tongue tip or an ellipse, with thin and rounded edges. Upon activation, the second driving assembly 41 controls the swinging blade 40 to perform the low-amplitude high-frequency swinging operation, and a swinging trajectory simulates the licking and sweeping actions of the tongue, and fits the user's sensitive body surface areas such as the neck, areas behind the ears, and inner thighs, thereby achieving a delicate massage experience similar to tongue licking. The lightweight design of the small-volume blade reduces the pressure on the skin, and offers a soft and smooth touch experience similar to that of the human tongue due to use of a super-soft silicone material; and the high-frequency small-amplitude swinging restores the flexible rhythm of tongue licking, which stimulates more real experience of natural human contact and reduces the mechanical stiffness during operation.

According to some embodiments of the present disclosure, optionally, as shown in FIGS. 1, 4, 6-7, and 10-12, the second massage assembly 4 further includes a contact ring wall 42; the contact ring wall 42 is connected to the housing 2; and the swinging blade 40 is disposed at a bottom of the contact ring wall 42.

The contact ring wall 42 may be of a detachable structure, and the user is allowed to replace ring walls of different specifications (such as different inner diameters, different contact densities or shapes) according to needs, which adapts to different body parts such as the neck and waist, facilitates separate cleaning and replacement, and prolongs the service life.

A micro vibration motor may be embedded into the contact ring wall 42, such that the contacts move synchronously with the swinging blade 40 to generate slight vibrations, thereby enhancing the multi-layered sensation and interactivity of the massage.

The contact ring wall 42 with an annular contour fits the skin, limits a motion range of the swinging blade 40, prevents the situation that the swinging blade 40 deviates from a target area during high-frequency swinging, and especially for an arc-shaped or irregular body surface, a framing effect of the contact ring wall 42 ensures that the swinging blade 40 always acts on a core massage point. The contacts of the contact ring wall 42 provide surrounding static or dynamic pressure stimulation, and the multi-layered sensation of peripheral wrapping and central tongue licking is formed together with the tongue-licking dynamic stimulation of the central swinging blade 40, which simulates the real massage experience of lip wrapping and tongue licking, enhances the richness of skin touch, and improves the authenticity of the bionic experience.

The present disclosure has been described with reference to preferred embodiments, but various modifications thereto may be made without departing from the scope of the present disclosure, and equivalents may be used to replace components therein. In particular, as long as there are no structural conflicts, various technical features mentioned in all embodiments may be combined in any manner. The present disclosure is not limited to specific embodiments disclosed herein but includes all technical solutions that fall within the scope of the claims.

What is claimed is:

1. An adult toy disinfection device, comprising:
a protective shell with an opening, wherein an inner cavity of the protective shell is a disinfection cavity;
a disinfection spectrum generation assembly; and
a first driving assembly; wherein
at least a portion of an adult toy can be placed in the disinfection cavity through the opening when the toy is to be disinfected;
the first driving assembly is electrically connected to the disinfection spectrum generation assembly and configured to drive the disinfection spectrum generation assembly to generate a disinfection spectrum;

the disinfection spectrum generation assembly is disposed on an inner side of the disinfection cavity, such that the disinfection spectrum directly irradiates or indirectly irradiates a space of the disinfection cavity by means of an optical path; and the disinfection cavity is provided with a spectral reflection layer disposed on an inner surface of the disinfection cavity, wherein the spectral reflection layer has multiple diffuse reflection structures with different diffuse reflection characteristics for different areas on the inner surface of the disinfection cavity.

2. The adult toy disinfection device according to claim 1, further comprising a light guide assembly comprising an incident port, an optical path, and an exit port;

the light guide assembly is disposed in the disinfection cavity, and the incident port is disposed at the disinfection spectrum generation assembly;

one or more exit ports are capable of being disposed at one or more key disinfection portions of the adult toy, wherein shapes of the one or more exit ports are adapted to shapes of the one or more key disinfection portions; and the optical path is configured to guide the disinfection spectrum incident from the incident port to exit through the exit port.

3. The adult toy disinfection device according to claim 2, further comprising a first motion platform carrying the light guide assembly for motion.

4. The adult toy disinfection device according to claim 1, wherein the first driving assembly has a first disinfection driving strategy;

the first disinfection driving strategy comprises a first driving program implemented by software and/or hardware circuits; and the first driving program is configured to drive a plurality of the disinfection spectrum generation assemblies corresponding to a plurality of key disinfection portions to light up one by one.

5. The adult toy disinfection device according to claim 1, further comprising a light condensing member and a light scanning assembly;

the disinfection spectrum forms a focused light spot through the light condensing member;

the light scanning assembly is configured to cause the focused light spot of the disinfection spectrum to perform scanning motion in an area (A); and the area (A) covers an area of the adult toy to be disinfected.

6. The adult toy disinfection device according to claim 5, wherein a plurality of the disinfection spectrum generation assemblies are arranged; and the plurality of the disinfection spectrum generation assemblies form a focused light spot through the same light condensing member.

7. The adult toy disinfection device according to claim 5, wherein the light scanning assembly is a motion platform carrying the disinfection spectrum generation assembly for motion.

8. The adult toy disinfection device according to claim 1, wherein an exhaust assembly is disposed in the disinfection cavity; and

water vapor inside the disinfection cavity is discharged outside the disinfection cavity through the exhaust assembly.

9. The adult toy disinfection device according to claim 1, further comprising a disinfection indication assembly;

the disinfection indication assembly is provided with a light-emitting unit; and the light-emitting unit is in an operating state during the disinfection process.

10. The adult toy disinfection device according to claim 9, wherein the operating state is one or more of breathing flash, color gradient flash, and chasing light flash.

11. An adult toy, comprising a housing, a battery, and a control circuit, further comprising:

a disinfection device;

a vibration massage assembly;

a second massage assembly;

the battery, the control circuit, and the massage assemblies are electrically connected;

the disinfection device comprises a disinfection spectrum generation assembly, a first driving assembly, and a protective shell with an opening, wherein an inner cavity of the protective shell is a disinfection cavity;

the vibration massage assembly and the second massage assembly are placed in the disinfection cavity through the opening, and the housing and the protective shell are combined to form an enclosed cavity; and the disinfection spectrum generation assembly is disposed on an inner side of the disinfection cavity, and the first driving assembly is configured to drive the disinfection spectrum generation assembly to generate a disinfection spectrum irradiating the space of the disinfection cavity.

12. The adult toy according to claim 11, wherein the housing comprises a first connecting portion; and the vibration massage assembly is detachably connected to the housing through the first connecting portion.

13. The adult toy according to claim 12, wherein the vibration massage assembly comprises a second connecting portion; and the second connecting portion flexibly connects the vibration massage assembly to the housing, and the vibration massage assembly is pulled through the second connecting portion.

14. The adult toy according to claim 13, wherein the second connecting portion comprises a wire; and the wire is configured to electrically connect the vibration massage assembly to the control circuit.

15. The adult toy according to claim 13, wherein the vibration massage assembly is of an insertable egg-shaped vibrator structure.

16. The adult toy according to claim 12, wherein the first connecting portion is a first cavity with a single open end, and the vibration massage assembly is connected to the housing in a way of being inserted into the first cavity; and and after the vibration massage assembly is inserted into the first cavity, a massage portion of the vibration massage assembly protrudes from the first cavity and achieves a massage function.

17. The adult toy according to claim 11, wherein the second massage assembly is fixedly connected to the housing, and the second massage assembly comprises a swinging blade and a second driving assembly; and the second driving assembly drives the swinging blade to swing to massage the user's massage area.

18. The adult toy according to claim 17, wherein the second massage assembly further comprises a contact ring wall;

the contact ring wall is connected to the housing; and the swinging blade is disposed at a bottom of the contact ring wall.

\* \* \* \* \*